(12) United States Patent
Suzuki

(10) Patent No.: US 9,072,670 B2
(45) Date of Patent: Jul. 7, 2015

(54) MATRIX-TYPE PHARMACEUTICAL SOLID PREPARATION

(75) Inventor: Kai Suzuki, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 179 days.

(21) Appl. No.: 12/738,543

(22) PCT Filed: Sep. 26, 2008

(86) PCT No.: PCT/JP2008/067996
§ 371 (c)(1),
(2), (4) Date: Apr. 16, 2010

(87) PCT Pub. No.: WO2009/051022
PCT Pub. Date: Apr. 23, 2009

(65) Prior Publication Data
US 2010/0233265 A1    Sep. 16, 2010

(30) Foreign Application Priority Data

Oct. 19, 2007  (JP) ................................. 2007-272700

(51) Int. Cl.
| | |
|---|---|
| A61K 9/14 | (2006.01) |
| A01N 43/04 | (2006.01) |
| A61K 31/70 | (2006.01) |
| A61K 9/16 | (2006.01) |

(52) U.S. Cl.
CPC ............ *A61K 9/1635* (2013.01); *A61K 9/1623* (2013.01)

(58) Field of Classification Search
None
See application file for complete search history.

(56) References Cited

U.S. PATENT DOCUMENTS

| | | | |
|---|---|---|---|
| 3,491,070 A * | 1/1970 | Weaver ...................... 526/307.2 |
| 4,968,508 A | 11/1990 | Oren et al. |
| 5,209,933 A | 5/1993 | MacFarlane et al. |
| 6,565,877 B1 * | 5/2003 | Mukherji et al. .............. 424/441 |
| 6,696,085 B2 | 2/2004 | Rault et al. |
| 6,946,156 B2 | 9/2005 | Bunick |
| 7,008,920 B2 * | 3/2006 | Kimura et al. ..................... 514/1 |
| 2002/0168404 A1 | 11/2002 | Rault et al. |
| 2003/0153608 A1 * | 8/2003 | Maegerlein et al. .......... 514/347 |
| 2004/0013697 A1 * | 1/2004 | Berndl et al. ................. 424/401 |
| 2004/0014817 A1 * | 1/2004 | Rosenberg et al. ........... 514/690 |
| 2004/0213849 A1 | 10/2004 | Sowden et al. |
| 2005/0196358 A1 | 9/2005 | Georgiades et al. |
| 2005/0196447 A1 | 9/2005 | Huang et al. |
| 2005/0202090 A1 | 9/2005 | Clarke |
| 2006/0134196 A1 * | 6/2006 | Rosenberg et al. ........... 424/464 |
| 2006/0159753 A1 | 7/2006 | Ueki et al. |
| 2007/0172523 A1 | 7/2007 | Hashitera et al. |
| 2007/0298103 A1 | 12/2007 | Hayes |
| 2008/0260815 A1 | 10/2008 | Hayes et al. |
| 2008/0280999 A1 | 11/2008 | Lakshman |

FOREIGN PATENT DOCUMENTS

| | | | |
|---|---|---|---|
| CN | 1638741 A | 7/2005 | |
| EP | 1413294 A1 | 4/2004 | |
| EP | 1 681 052 A1 | 7/2006 | |
| JP | 04-043049 A | 2/1992 | |
| JP | 06-024991 A | 2/1994 | |
| JP | 06-199657 A | 7/1994 | |
| JP | 11-5739 A | 1/1999 | |
| JP | 2005-206490 A | 8/2005 | |
| WO | 92/13880 A1 | 8/1992 | |
| WO | 96/14058 A1 | 5/1996 | |
| WO | 99-17742 A2 | 4/1999 | |
| WO | 99/52528 A1 | 10/1999 | |
| WO | 99-63971 A1 | 12/1999 | |
| WO | 00-15261 A1 | 3/2000 | |
| WO | 03-057197 A1 | 7/2003 | |
| WO | 03/082204 A2 | 10/2003 | |
| WO | 2005/000310 A1 | 1/2005 | |
| WO | 2005/079760 A1 | 9/2005 | |
| WO | 2006/024881 A2 | 3/2006 | |
| WO | WO 2006/063737 * | 6/2006 | ......... A61K 31/4184 |
| WO | 2007/000779 A2 | 1/2007 | |
| WO | WO2007/000779 * | 1/2007 | ............... A61K 9/20 |
| WO | 2007-085024 A2 | 7/2007 | |
| WO | 2007/106182 A2 | 9/2007 | |

OTHER PUBLICATIONS

Aleksey Drozdov, Viscoelastoplasticity of Amorphous Glassy Polymers, 36 Eur. Polymer J 2063 (2000).*
T. T Kotani, J. Sweeny & I.M. Ward, the Measurement of Transverse Mechanical Properties of Polymer Fibres, 29 J Mat. Sci. 5551 (1994).*
Tesconi et al (1999). "The Preparation of Soft Gelatin Capsules for a Radioactive Tracer Study." Pharmaceutical Development and Technology, 4(4): 507-513).*
Doggrell, Sheila. (2004). "Tolvaptan Otsuka." Current Opinion in investigation Drug, 5(9): 977-983.*
Ketan A. Mehta et al., "Release performance of a poorly soluble drug from a novel, Eudragit®-based multi-unit erosion matrix", International Journal of Pharmaceutics, 2001, vol. 213, pp. 7-12.
Notice of Opposition dated Jan. 10, 2014, filed by Sandoz AG over EP Patent No. 2180882.
Notice of Opposition dated Jan. 10, 2014, filed by Agrobiogen GmbH Biotechnologie over EP Patent No. 2180882.
Cameron, Claud G., et al., "Controlled-Release Theophylline Tablet Formulations Containing Acrylic Resins, III. Influence of Filler Excipient," Drug Development and Industrial Pharmacy, vol. 13, No. 2, 1987, pp. 303-318.
Pharma Polymer News, vol. 10, 2003, pp. 1-4.
"Acrylic polymers for solid oral dosage forms", Eudragit®—overview.

(Continued)

*Primary Examiner* — Anoop Singh
*Assistant Examiner* — Doan Phan
(74) *Attorney, Agent, or Firm* — Sughrue Mion, PLLC

(57) ABSTRACT

The present invention aims to provide a matrix-type solid preparation that has high-level release controllability for suppressing drug release in the upper gastrointestinal tract and accelerating drug release in the lower gastrointestinal tract, and that solves of all the above drawbacks caused by combining a plasticizer. The present invention provides a matrix-type pharmaceutical solid preparation that contains: (a) a methacrylic acid-based enteric polymer; and (b) a sugar and/or a sugar alcohol, wherein 1 g of the sugar and/or the sugar alcohol can be dissolved in not more than 4 g of water at a water temperature of 20 to 25° C.

4 Claims, 2 Drawing Sheets

(56) References Cited

OTHER PUBLICATIONS

Young, Christopher R., et al., "Compression of Controlled-Release Pellets Produced by a Hot-Melt Extrusion and Spheronization Process," Pharmaceutical Development and Technology, vol. 1, 2005, pp. 133-139.

Takeuchi, Hirofumi, et al., "Controlled Release Theophylline Tablet with Acrylic Polymers Prepared by Spray-Drying Technique in Aqueous System," Drug Development and Industrial Pharmacy, vol. 15, No. 12, 1989, pp. 1999-2016.

Henrist, D., et al., "Influence of the formulation composition on the in vitro characteristics of hot stage extrudates," International Journal of Pharmaceutics., vol. 188, 1999, pp. 111-119.

Mathew, Aji P., et al. "Plasticized Waxy Maize Starch: Effect of Polyols and Relative Humidity on Material Properties," Biomacromolecules, vol. 3, 2002, pp. 1101-1108.

"Table I. Uses of sorbitol," Pharmaceutical Excipients, Pharmaceutical Press, London, accessed on Dec. 12, 2013.

"Polyols," Cargill.

Ghanbarzadeh et al., "Investigation of Water Vapour Permeability, Hydrophobicity and Morphology of Zein Films Plasticized by Polyols," Iranian Polymer Journal, vol. 15 (9), 2006, pp. 691-700.

Shaw, N.B., et al., "Physical Properties of WPI Films Plasticized with Glycerol, Xylitol, or Sorbitol," Journal of Food Science 2002, vol. 67(1), pp. 164-167.

Official Journal of the European Communities, 1992, vol. 35, A54-A62.

Behera A.L., et al., "Enhancement of Solubility: A Pharmaceutical Overview," Der Pharmacia Lettre, 2010, 2(2), pp. 310-318.

C. Thompson, "Bonding," Pharmaceutics (part I), pp. 21-30, Spring 2004.

Rowe, et al., Handbook of Pharmaceutical Excipients, 4th Ed., pp. 323-332 (2003).

\* cited by examiner

MATRIX-TYPE PHARMACEUTICAL SOLID PREPARATION

TECHNICAL FIELD

The present invention relates to a pharmaceutical solid preparation.

BACKGROUND OF THE INVENTION

There have been many attempts in the medical field to control drug release and maintain drug concentration in the blood at an appropriate level for a long period of time. In order to maintain drug concentration in the blood at an appropriate level for a long period of time, it is necessary for maintaining the absorption of drugs for a long time to use the pharmaceutical ingenuities (sustained-release techniques). Orally administered solid preparations are moved from the upper part of the gastrointestinal tract (the stomach and upper small intestine) to the lower part (the lower small intestine and large intestine) as time passes; the capability of drug absorption is often less in the lower part of the gastrointestinal tract than in the upper part. Therefore, it is considered most important to develop a strategy by which the drug can be continuously absorbed in the lower gastrointestinal tract, in which the solid preparation remains for the longest time.

Known sustained-release techniques include, for example, a sustained-release technique based on diffusion control, i.e., membrane-coated preparations in which core compositions or core tablets that contain drugs are coated with water-insoluble polymer films; matrix preparations produced together with water-insoluble polymers, waxes, etc.; and the like. However, with these techniques, since the release rate of the drug decreases as the release progresses, the drug release rate is deficient in the lower gastrointestinal tract, to which the preparation reaches several hours after administration. As a result, the drug concentration in the blood is hard to maintain.

Another known sustained-release technique adopts the pharmaceutical approach designed to release the drug in the lower gastrointestinal tract (e.g., enteric coated preparations in which immediate release core compositions containing drugs are coated with enteric films). However, this technique controls the drug release with films, and hence requires a film-coating procedure. As a result, the production process of the pharmaceutical preparation becomes complicated.

On the other hand, sustained-release matrix preparations are known that are produced using methacrylic acid-based enteric polymers. The enteric polymer becomes an insoluble substance at a lower pH range than the pH at which the enteric polymer can be dissolved, and becomes a soluble substance at a higher pH range than the pH at which the enteric polymer can be dissolved. Therefore, the enteric polymer-containing matrix preparation can suppress drug release in the upper gastrointestinal tract and rapidly release the drug in the lower gastrointestinal tract. In other words, sensitive pH response of the enteric polymer enables the provision of sustained-release preparations with precisely controlled drug release.

For example, Patent Documents 1, 2, 3, and 4 disclose enteric polymer-containing matrix preparations obtained by mixing an enteric polymer and a drug, followed by a compaction (tablet compression). However, although drug release from matrix preparations is generally considered to be dependent on the surface area of the pharmaceutical preparation, such matrix preparations obtained by tablet compression have a small surface area in contact with a solvent. For poorly soluble drugs with a slow dissolution rate, the small surface area of the pharmaceutical preparation induces deficiency in drug release.

In contrast, Patent Document 5 discloses preparations obtained by wet-kneading a mixed powder containing methacrylic acid copolymer S with ethanol, followed by extrusion. This preparation is formed into sustained-release pellets through wet-kneading and extrusion. Such a preparation (pellets, granules, and powder are referred to as multiple-unit type preparations) can have a larger surface area and is also applicable to poorly-soluble drugs. Furthermore, as compared with single-unit type preparations such as tablets obtained by tablet compression, multiple-unit type preparations like pellets are moderately dispersed in the gastrointestinal tract. Therefore, such pellets can reduce inter-subject variance in drug absorption rather than the tablets.

Moreover, Non-Patent Document 1 discloses multiple-unit type preparations comprised of methacrylic acid copolymer S, methacrylic acid copolymer LD, a drug, polyvinylpyrrolidone, and triethyl citrate, as a plasticizer. The preparations are obtained by wet-kneading with water, and followed by extrusion and spheronization.

Patent Document 1: Japanese Examined Patent Publication No. 1992-43049
Patent Document 2: Japanese Unexamined Patent Publication No. 1994-199657
Patent Document 3: U.S. Pat. No. 4,968,508
Patent Document 4: US Patent Publication No. 2006-0159753
Patent Document 5: Japanese Unexamined Patent Publication No. 1994-24991
Non-Patent Document 1: International Journal of Pharmaceutics, 2001, Vol. 213, p. 7-12

DISCLOSURE OF THE INVENTION

However, as described below, there are problems in the process that produces pellets or granules by processing a mixture containing the above-mentioned enteric polymer by extrusion and spheronization.

First, the methacrylic acid-based enteric polymer is a hard enteric polymer, as expected from its high glass transition temperature of not less than 160° C. For this reason, when matrix preparations containing methacrylic acid-based enteric polymers are produced by an extrusion and spheronization, the wet-kneaded product must be supplemented with plasticity so that extrusion may be performed smoothly.

Although the proportion of the methacrylic acid copolymer S in the pharmaceutical composition prepared by the technique of Patent Document 5 is 5 wt. %, the amount of the methacrylic acid copolymer S in the composition must be increased in order to enhance the pH response of the obtained pharmaceutical preparation further. However, the increased amount of methacrylic acid copolymer S in the composition results in insufficient plasticity, making it difficult to produce matrix preparations containing methacrylic acid-based enteric polymers by the extrusion and spheronization method. More specifically, such insufficient plasticity increases resistance when the wet-kneaded product is extruded. As a result, the extrusion can not be performed.

On the other hand, the pharmaceutical composition prepared by the technique of Non-Patent Document 1 contains 77 wt % of the methacrylic acid copolymer, and about 11 wt. % of triethyl citrate is added as a plasticizer to supplement plasticity necessary to extrude a wet-kneaded product. However, with this technique, the glass transition temperature of the methacrylic acid-based enteric polymer is lowered due to the addition of a plasticizer, resulting in metamorphosis and deformation of the methacrylic acid based-enteric polymers. Accordingly, a film may be formed inside the screen die of the extruder that possibly causes the obstruction or failure of it. Moreover, the metamorphosis and deformation of the methacrylic acid-based enteric polymers with time and dissolution change of the obtained preparations with time may possibly result because of the remaining plasticizer in the obtained preparations. Furthermore, the technique of Non-Patent Document 1 has a concern of an incompatibility with drugs.

Thus, a plasticizer is necessary to increase the proportion of the methacrylic acid-based enteric polymer in the obtained preparation by extrusion, whereas the addition of a plasticizer causes unavoidable problems, as described above. In other words, it is quite difficult to increase the proportion of the enteric polymer in the obtained preparation by extrusion, while solving the problems resulting from the addition of a plasticizer.

The present invention provides a pharmaceutical solid preparation that is free from the above-described problems of the conventional techniques, even though the compounding ratio of the methacrylic acid-based enteric polymer with good pH response is increased to impart sustained-release properties to the preparation.

More specifically, an object of the present invention is to provide matrix-type solid preparations that overcome all the above problems caused by adding a plasticizer, while having the advanced release controllability capable of suppressing drug release in the upper gastrointestinal tract and immediately releasing the drug in the lower gastrointestinal tract.

The present inventor conducted extensive research to solve the above problems, and found that desired matrix-type solid preparations can be obtained by a combination of a methacrylic acid-based enteric polymer and a sugar and/or a sugar alcohol having a specific property. The present invention has been accomplished based on these findings.

The present invention provides the matrix-type pharmaceutical solid preparation, as defined in the following Items 1 to 9.

Item 1: The matrix-type pharmaceutical solid preparation comprising: (a) a methacrylic acid-based enteric polymer; and (b) a sugar and/or a sugar alcohol, wherein 1 g of the sugar and/or the sugar alcohol (b) can be dissolved in not more than 4 g of water at a certain point of water temperature between 20 to 25° C.

Item 2: The pharmaceutical solid preparation according to Item 1, wherein the amount of the sugar and/or the sugar alcohol is 0.1 to 10 parts by weight based on 1 part by weight of the methacrylic acid-based enteric polymer.

Item 3: The pharmaceutical solid preparation according to Item 1 or 2, wherein the sugar and/or the sugar alcohol have a melting point of 140° C. or less.

Item 4: The pharmaceutical solid preparation according to Item 1 or 2, being free from a plasticizer.

Item 5: The pharmaceutical solid preparation according to Item 3, being free from a plasticizer.

Item 6: The pharmaceutical solid preparation according to Item 1 or 2, being prepared by a production method including an extrusion process.

Item 7: The pharmaceutical solid preparation according to Item 3, being prepared by a production method including an extrusion process.

Item 8: The pharmaceutical solid preparation according to any one of Items 1 to 7, wherein the sugar and/or the sugar alcohol are at least one member selected from the group consisting of erythritol, xylitol, lactitol, sorbitol, trehalose, and maltose, dextrose, fructose, and maltitol.

Item 9: The pharmaceutical solid preparation according to Item 1, wherein the content of the methacrylic acid-based enteric polymer is 6 to 50 wt. %.

Item 10: The pharmaceutical solid preparation according to Item 1, wherein the methacrylic acid-based enteric polymers are dissolved the property of dissolved at pH 5.5 or above.

Item 11: The pharmaceutical solid preparation according to Item 1, wherein the methacrylic acid-based enteric polymer has a glass transition temperature of not less than 100° C.

Item 12: The pharmaceutical solid preparation according to any one of Items 1 to 11, wherein the methacrylic acid-based enteric polymer is at least one member selected from the group consisting of methacrylic acid copolymer L, methacrylic acid copolymer LD, and methacrylic acid copolymer S.

Item 13: The pharmaceutical solid preparation according to Item 1 comprising a drug selected from the group consisting of cilostazol, tolvaptan, phenyloin, aspirin and naproxen.

Pharmaceutical Solid Preparation

The matrix-type pharmaceutical solid preparation of the present invention comprises (a) a methacrylic acid-based enteric polymer and (b) a sugar and/or a sugar alcohol.

The sugar and/or the sugar alcohol (b) have the property that 1 g of them can be dissolved in not more than 4 g water at a certain point of water temperature between 20 to 25° C.

The pharmaceutical solid preparation of the invention may contain other components, preferably (c) a drug and (d) a form-maintaining material, in addition to the above components (a) and (b). The pharmaceutical solid preparation does not contain a plasticizer.

The pharmaceutical solid preparation is preferably a matrix-type oral sustained-release pharmaceutical solid preparation.

(a) Methacrylic Acid-Based Enteric Polymer

In the invention, as the methacrylic acid-based enteric polymer (a), a wide range of known methacrylic acid-based enteric polymers can be used as long as they are soluble in the pH environment of the lower small intestine and the large intestine. Suitable methacrylic acid-based enteric polymers are dissolved at a pH of 5.5 or above, more preferably 6.0, and at a pH of 7.5 or below. When the dissolution pH is in this range, the enteric polymer is dissolved in the small intestine and/or the large intestine, which allows for the rapid release of the drug from the preparation in the lower gastrointestinal tract.

Moreover, in the invention, the glass transition temperature of the methacrylic acid-based enteric polymer is generally 100° C. or higher, preferably 105° C. or higher, more preferably 130° C. or higher. The glass transition temperature is preferably 200° C. or lower. At the glass transition temperature in this range, deformation and metamorphosis do not occur at room temperature, leading to less concern about a dissolution change of the preparation with time. Another advantage is that extrusion can be carried out without imposing an excessive load on the extruder.

Suitable specific examples of the methacrylic acid-based enteric polymer include methacrylic acid copolymer LD, methacrylic acid copolymer L, methacrylic acid copolymer S, and the like. Methacrylic acid copolymer LD preferably takes the form of powders. The powdery methacrylic acid copolymer LD indicates a polymer neither in liquid form nor in the form of a suspension with 30% solid content. Moreover, the methacrylic acid copolymer LD to be used in the invention may be in a dry state or, even when some moisture is contained, in powder form. Hereinafter, such a powdery methacrylic acid copolymer LD is occasionally referred to as a dry methacrylic acid copolymer LD.

As the methacrylic acid-based enteric polymers, any easily available commercial products are usable. For example, "Eudragit L100D55" (Degussa AG) may be used as the dry methacrylic acid copolymer LD, "Eudragit L100" (Degussa AG) as the methacrylic acid copolymer L, and "Eudragit S100" (Degussa AG) as the methacrylic acid copolymer S, respectively. These enteric polymers may be used singly or in a combination of two or more.

Mixing two or more of these enteric polymers can arbitrarily determine a pH in the range of 5.5 to 7 at which the preparation is dissolved in the lower small intestine and the large intestine (dissolution pH of the enteric polymer). For example, when the dissolution pH of the enteric polymer is arbitrarily determined in the range of 5.5 to 6, the mixing ratio of methacrylic acid copolymer LD to methacrylic acid copolymer L may be in the range of 1:99 to 99:1. Moreover, when the dissolution pH of the enteric polymer is arbitrarily determined in the range of 5.5 to 7, the mixing ratio of methacrylic acid copolymer LD to methacrylic acid copolymer S may be in the range of 1:99 to 99:1. Furthermore, when the dissolution pH of the enteric polymer is arbitrarily determined in the range of 6 to 7, the mixing ratio of methacrylic acid copolymer L to methacrylic acid copolymer S may be in the range of 1:99 to 99:1.

In the invention, the amount of the enteric polymer to be contained in the preparation is generally 1 to 50 wt. %, preferably 3 to 45 wt. %, more preferably 6 to 40 wt. %, and even more preferably 10 to 35 wt. %. The content of the enteric polymer in this range is preferable in terms of the variety of drug release patterns and production suitability (excellent extrusion). Here, the variety of drug release patterns means that a designer of the preparation can easily achieve an intended drug release pattern.

The methacrylic acid-based enteric polymer used for the pharmaceutical solid preparation of the invention is preferably dissolved at a pH of 5.5 or above. The pH response to be given to the pharmaceutical solid preparation of the invention is suitably adjusted by the variety of the drugs listed below, desired pharmacologic effects, etc. The pH response can also be adjusted by the variety of methacrylic acid-based enteric polymers used, the amount of the enteric polymer contained in the preparation, etc.

For example, some preparations are preferably designed to slowly release the drugs in the upper gastrointestinal tract (the stomach and upper small intestine), in addition to the function of the preparations to be continuously absorbed in the lower gastrointestinal tract (the lower small intestine and large intestine). In such cases, it is desirable to soften the pH response of the pharmaceutical solid preparation. Specifically, the amount of the methacrylic acid-based enteric polymer contained in the pharmaceutical solid preparation is set smaller.

Moreover, when enhancing the function of the preparation to be continuously absorbed in the lower gastrointestinal tract, it is desirable to sharpen the pH response of the pharmaceutical solid preparation. Specifically, the amount of the methacrylic acid-based enteric polymer contained in the pharmaceutical solid preparation is set larger.

(b) Sugar and/or Sugar Alcohol

The sugar and/or the sugar alcohol used in the invention have a specific solubility to water. The amount of water at a certain point of water temperature between 20 to 25° C. necessary to dissolve 1 g of sugar and/or sugar alcohol is generally 4 g or less, preferably 3.5 g or less. Moreover, the amount of water at a certain point of water temperature between 20 to 25° C. necessary to dissolve 1 g of sugar and/or sugar alcohol is desirably 1 g or more. When the amount of water necessary for dissolution is in this range, proper plasticity can be provided to the kneaded mixture prior to the production of the preparation.

More preferable sugar and/or sugar alcohol have a melting point of 140° C. or lower, preferably 130° C. or lower, more preferably 125° C. or lower, and 90° C. or higher. With a melting point of this range, the sugar and/or the sugar alcohol can take a solid form at room temperature, providing easy handling. Another advantage is that the hardness of the sugar and/or sugar alcohol has no affect on the extrusion.

The sugar and/or the sugar alcohol usable in the invention may be those having such properties, and may be in a form of hydrate(s). Examples thereof include at least one member selected from the group consisting of erythritol, xylitol, lactitol, sorbitol, trehalose, maltose, dextrose, fructose, maltitol. Preferable examples include at least one member selected from the group consisting of erythritol, xylitol, lactitol, sorbitol, trehalose, maltose, dextrose, fructose, maltitol. More preferable sugars and/or sugar alcohols may be at least one member selected from the group consisting of erythritol, xylitol, lactitol, sorbitol, trehalose, maltose. Even more preferable sugars and/or sugar alcohols may be at least one member selected from the group consisting of erythritol, lactitol monohydrate, trehalose dihydrate, and maltose monohydrate. These even more preferable sugars and/or sugar alcohols have reasonable solubility and an appropriate melting point, as well as less concern about hygroscopicity. They also have excellent long-term storage stability.

The sugar and/or sugar alcohol can be selected from a variety of commercial products. More specific examples are listed below.

(B-i) Erythritol and Hydrates Thereof

Erythritol, i.e., a sugar alcohol, is produced from glucose by enzyme reaction. The melting point of erythritol is 119 to 122° C., and the amount of water (25° C.) necessary to dissolve 1 g of erythritol is 3.3 g (Nikken Chemicals Co., Ltd., Erythritol Technical Data). As erythritol, commercial products such as "Erythritol 100M" (Nikken Chemicals Co., Ltd.) can be used.

(B-ii) Xylitol and Hydrates Thereof

Xylitol, i.e., a sugar alcohol, is produced by converting various cellulose raw materials into xylose by hydrolysis, followed by hydrogenation. Xylitol has some hygroscopicity. The amount of water (20° C.) necessary to dissolve 1 g of xylitol is 1.6 g (Handbook of Pharmaceutical Excipients, 2001, Japan Pharmaceutical Excipients Council). Further, the melting point of xylitol is 93 to 95° C. (Handbook of Pharmaceutical Excipients, 2001, Japan Pharmaceutical Excipients Council). As xylitol, commercial products such as "xylitol P" (Nikken Fine Chemical Co., Ltd.), "XYLISORB" (Roquette) and "Xylit P" (Towa Chemical Industry Co., Ltd.) can be used.

(B-iii) Lactitol and Hydrates Thereof

Lactitol, i.e., a sugar alcohol, is produced by catalytic hydrogenation of lactose. Examples of lactitol include anhydride, monohydrate, dihydrate, and trihydrate. Among them, non-hygroscopic monohydrate is preferable. The melting point of lactitol monohydrate is 97° C. (Merck Index, 12th edition), and the amount of water (20° C.) necessary to dissolve 1 g of lactitol is 1.8 g (Handbook of Pharmaceutical Excipients, 2001, Japan Pharmaceutical Excipients Council). As lactitol monohydrate, commercial products such as "Lactitol LC-1" (Nikken Fine Chemical Co., Ltd.) can be used.

(B-iv) Sorbitol and Hydrates Thereof

Sorbitol, i.e., a sugar alcohol, is produced by subjecting glucose or corn syrup to high pressure hydrogenation or electrolytic reduction. Sorbitol has high hygroscopicity. The amount of water (25° C.) necessary to dissolve 1 g sorbitol is 0.5 ml (g) (Handbook of Pharmaceutical Excipients, 2001, Japan Pharmaceutical Excipients Council). Further, the melting point of sorbitol is 97 to 112° C. (Handbook of Pharmaceutical Excipients, 2001, Japan Pharmaceutical Excipients Council; Journal of Thermal Analysis and Calorimetry, Vol. 73, p. 615-621). As sorbitol, commercial products such as "Sorbitol SP" (Nikken Fine Chemical Co., Ltd.), "NEOSORB Powder" (Roquette), and "Sorbitol DP-10M" (Towa Chemical Industry Co., Ltd.) can be used.

(B-v) Trehalose and Hydrates Thereof

Trehalose dihydrate, i.e., a sugar component, is a disaccharide in which two glucoses are bound, similar to maltose. Trehalose as a pharmaceutical additive is produced from a partial starch degradation product by an enzyme method using trehalose-producing bacteria. Although trehalose dihydrate is not non-hygroscopic, it does have low hygroscopicity. The melting point of trehalose dihydrate is 97° C., and the amount of water (20° C.) necessary to dissolve 1 g of trehalose dihydrate is 1.2 g (Trehalose Technical Data, Hayashibara Biochemical Labs., Inc.). As trehalose dihydrate, commercial products such as "Trehalose P" (Asahi Kasei Chemicals Corp.) and "Treha" (Hayashibara Co., Ltd) can be used.

(B-vi) Maltose and Hydrates Thereof

Maltose monohydrate, i.e., a sugar component, is a disaccharide carbohydrate, which is produced by enzymolysis of starch. When the maltose content is 90% or higher, it can be also used for pharmaceutical preparations as maltose syrup powder in a pharmaceutical additive. Maltose is divided into anhydride and monohydrate, and monohydrate has low hygroscopicity. The amount of water (20° C.) necessary to dissolve 1 g of maltose monohydrate is 1.2 g (New Food Industry, Vol. 31, No. 4, p. 17-22). Further, the melting point (decomposition) of maltose monohydrate is 102 to 103° C. (Handbook of Pharmaceutical Excipients, 2001, Japan Pharmaceutical Excipients Council). As maltose monohydrate, commercial products such as "Sunmalt-S" (Sanwa Cornstarch Co., Ltd.) and "Nisshoku Crystal Maltose" (Nihon Shokuhin Kako Co., Ltd.) can be used.

In the invention, mixing the sugar and/or the sugar alcohol (b) can enhance the plasticity of the kneaded mixture containing methacrylic acid-based enteric polymers, without using a plasticizer. Since the invention is plasticizer-free, various harmful influences caused by the use of a plasticizer can be avoided. Accordingly, the stability of the preparation can be improved and the dissolution properties of the drug can be easily controlled.

In the invention, as for the content ratio of methacrylic acid-based enteric polymer to sugar and/or sugar alcohol, the content of sugar and/or sugar alcohol is usually 0.01 to 20 parts by weight, preferably 0.1 to 10 parts by weight, more preferably 0.2 to 5 parts by weight, based on 1 part by weight of methacrylic acid-based enteric polymer. The amount of sugar and/or sugar alcohol in this range is preferable because the preparation is easier to handle and take, the plasticity of the kneaded mixture is enhanced, and production suitability (ease of production) is achieved.

Regarding the other sugar and/or sugar alcohol specifically described above, the melting point thereof and the amount of water necessary to dissolve 1 g of sugar and/or sugar alcohol are 160 to 186° C. and 0.5 g for sucrose, 83° C. and 1 g for dextrose, 102 to 105° C. and 0.3 g for fructose, and 148 to 151° C. and easily soluble for maltitol (Handbook of Pharmaceutical Excipients, 2001, Japan Pharmaceutical Excipients Council).

(c) Drugs

Any drugs are usable as long as they serve as a medicinal active ingredient to treat or prevent diseases. Such drugs can be used in the forms of a free body, a salt thereof, a solvate (hydrate, ethanol solvate, etc.), or a crystal polymorphism. Suitable drugs to be used in the invention are such that the occurrence of side effects is reduced by the sustained-release technique of the invention to enhance therapeutic efficacy. Further, suitable drugs are such that immediate drug release leads to enhanced therapeutic efficacy for Crohn's disease, ulcerative colitis, irritable colitis, colon cancer, and like diseases that damage the lower gastrointestinal tract.

The drugs may be crystalline or non-crystalline. The drugs may be water-soluble or lipid-soluble, and may be poorly soluble in water as well. The drugs are preferably weakly basic, neutral, or acid.

When using poorly soluble drugs, nanomization, micronization, amorphization, and like pharmaceutical techniques may be used to improve the solubility of the poorly soluble drugs. However, with the technique of wet-kneading with ethanol, as described in the background art of Patent Document 5, ethanol could potentially trigger problems like crystallization or crystal-growth of drugs.

Examples of drugs used in the invention include 5-aminosalicylic acid, acyclovir, aspirin, acetylsalicylic acid, acetaminophen, aripiprazole, ampicillin, isoniazid, ibuprofen, indomethacin, ethenzamide, enalapril, erythromycin, omeprazole, ketoconazole, salbutamol, salazosulfapyridine, salazopyrin, diazepam, diclofenac, diclofenac sodium, dipyridamole, cimetidine, cilostazol, simvastatin, sucralfate, sulpiride, sulfasalazine, celecoxib, tacrolimus, theophylline, tegafur, dexamethasone, dextromethorphan, tetomilast, terfenadine, doxorubicin, triamcinolone, tolvaptan, nadifloxacin, naproxen, nifedipine, urea, sodium valproate, haloperidol, valaciclovir, paliperidone, hydrocortisone, famotidine, phenacetin, phenyloin, phenylpropanolamine, budesonide, pravastatin, pravastatin sodium, fluorouracil, prednisolone, prednisone, furosemide, probucol, vesnarinone, penicillin, perphenazine, chlorpheniramine maleate, midazolam, doxazosin mesilate, methotrexate, morphine, ranitidine, lansoprazole, lisinopril, risperidone, lidocaine, rebamipide, levodopa, rotigotine, lovastatin, lorazepam, warfarin, ambroxol hydrochloride, carteolol hydrochloride, diphenhydramine hydrochloride, tamsulosin hydrochloride, nicardipine hydrochloride, hydralazine hydrochloride, buprenorphine hydrochloride, procaterol hydrochloride, mozavaptane hydrochloride, ranitidine hydrochloride, levocarnitine hydrochloride, cortisone acetate, salbutamol sulfate, and the like.

Preferable drugs are 5-aminosalicylic acid, acyclovir, aspirin, acetylsalicylic acid, acetaminophen, aripiprazole, ibuprofen, indomethacin, ethenzamide, omeprazole, salazosulfapyridine, salazopyrin, diazepam, diclofenac, diclofenac sodium, dipyridamole, cilostazol, simvastatin, tacrolimus, theophylline, tegafur, tetomilast, doxorubicin, tolvaptan, haloperidol, paliperidone, hydrocortisone, phenyloin, budesonide, pravastatin, fluorouracil, prednisolone, prednisone, furosemide, probucol, vesnarinone, lansoprazole, risperidone, rebamipide, levodopa, rotigotine, lovastatin, carteolol hydrochloride, nicardipine hydrochloride, procaterol hydrochloride, mozavaptane hydrochloride, cortisone acetate, salbutamol sulfate, and the like. More preferable ones are cilostazol, tolvaptan, phenyloin, aspirin, and naproxen.

The amount of these drugs contained in the pharmaceutical preparation is generally 1 to 90 wt. %, preferably 5 to 80 wt.

%, more preferably 10 to 70 wt. %. These drugs may be used singly or in a combination of two or more in the pharmaceutical preparation of the invention.

In the invention, the sustained-release pharmaceutical solid preparations produced by using these drugs allow about one or two times administration a day. For example, tolvaptan has the following effects as a vasopressin antagonistic activity: vasodilating activity, hypotensive activity, activity for inhibiting saccharide release in liver, activity for inhibiting growth of mesangium cells, water diuretic activity, platelet agglutination inhibitory activity, inhibitory activity for vomiting, activity for promoting urea excretion, inhibitory activity on secretion of factor VIII, activity for promoting heart function, activity for inhibiting constriction of mesangium cells, inhibitory activity on production of saccharide in liver, inhibitory activity on aldosterone secretion, inhibitory activity on production of endotheline, regulation activity on renin secretion, memory regulation activity, thermoregulation activity, activity for regulating production of prostaglandin, etc. Tolvaptan advantageously serves as a vasodilators, hypotensive agents, water diuretics, platelet agglutination inhibitors, promoters for urea excretion, agent for heart failure, agent for renal failure, etc.; and it is effective in preventing and/or treating hypertension, edema, ascites, heart failure, renal function disorder, vasopressin parasecretion syndrome (SIADH), hepatocirrhosis, hyponatremia, hypokalemia, diabetes, circulation disorder, motion sickness, water metabolism disorder, renal failure, various diseases associated with ischemic, etc. Moreover, tolvaptan has the following effects as oxytocin antagonistic activities: inhibitory effect on uterine smooth muscle constriction, inhibitory effect on milk secretion, inhibitory effect on synthesis and secretion of prostaglandin, and vasodilating activity; additionally, it is effective in preventing and/or treating oxytocin-associated diseases, particularly premature delivery, dysmenorrhea, or in stopping labor preparatory to Caesarean delivery, etc. Tolvaptan is also effective in preventing and/or treating polycystic kidney diseases. Using these drugs, the sustained-release technique of the invention can produce preparations that are administered once a day.

(d) Form-Maintaining Materials

In the invention, the form-maintaining material (d) may be those that maintain desired forms of the preparation during production in various production processes. Preferable materials are those that maintain the form of pharmaceutical preparations produced by the extrusion and spheronization method.

In the invention, desirable materials for the form-maintaining material (d) are water-retentive, swellable, and plastic. Examples of form-maintaining materials used include hydroxypropylcellulose, hypromellose, methylcellulose, hydroxyethylcellulose, and like water-soluble cellulose; crystalline cellulose, low-substituted hydroxypropyl cellulose, carmellose, carmellose calcium, carmellose sodium, croscarmellose sodium, carboxymethylethylcellulose, ethylcellulose, hypromellose phthalate, hydroxypropylmethylcellulose acetate phthalate, cellulose acetate, cellulose acetate phthalate, and like water-insoluble cellulose; polyvinyl pyrrolidone, polyethylene oxide, carboxyvinyl polymer, polyvinyl alcohol (partially or fully saponified), and like water-soluble synthetic polymers; crospovidone, polycarbophil, polycarbophil calcium, aminoalkyl methacrylate copolymer E, aminoalkyl methacrylate copolymer RS, methacrylic acid copolymer L, methacrylic acid copolymer S, methacrylic acid copolymer LD, dry methacrylic acid copolymer LD, polyvinylacetal diethylaminoacetate, and like water-insoluble synthetic polymers; wheat starch, rice starch, corn starch, potato starch, partially pregelatinized starch, pregelatinized starch, dextrin, α-cyclodextrin, β-cyclodextrin, maltodextrin, isomalt, hydroxypropyl starch, sodium carboxymethyl starch, pullulan, and like starches; gum arabic, gum arabic powder, agar, agar powder, gelatin, purified gelatin, chitosan, xanthan gum, pectin, sodium alginate, locust bean gum, guar gum, and like natural polymer compounds; stearic acid, monoglycerol stearate, carnauba wax, stearyl alcohol, cetanol, macrogol 1500, macrogol 4000, macrogol 6000, and like low-melting-point substances; and the like. These form-maintaining materials are used singly or in a combination of two or more.

Preferable form-maintaining materials are water-insoluble and have less disintegration action. Examples of such form-maintaining materials include crystalline cellulose, chitosan, sodium alginate, polycarbophil, polycarbophil calcium, etc. Crystalline cellulose is most preferable.

As crystalline cellulose, commercial products such as "Ceolus PH-101", "Ceolus PH-102", "Ceolus PH-301", "Ceolus PH-302", and "Ceolus KG-802" (Asahi Kasei Chemicals Corp.), "Avicel PH-200" (FMC Corporation), "VIVAPUR 12" (JRS), etc. can be used.

The amount of these form maintaining materials contained in the pharmaceutical preparation is generally 1 to 90 wt. %, preferably 3 to 80 wt. %, more preferably 5 to 50 wt. %.

Other Components

The pharmaceutical preparation of the invention may contain, for example, excipients, binders, pH adjustors, absorption enhancers, lubricants, colorants, corrigents, flavors, capsules, and like various additives that can be mixed with the solid pharmaceutical preparation. These components may be mixed in the pharmaceutical preparation of the invention in an amount that does not impair the effects of the invention.

The pharmaceutical solid preparation of the invention is preferably produced through the extrusion method and spheronization method. The dosage form thereof is preferably powders, pellets, and capsules. Moreover, the pharmaceutical solid preparation of the invention may be formed in such a manner that the above powders or pellets is contained in tablets, similar to space tab-type tablets (pellet-containing tablets) as described in Advancing Medication, Forefront of DDS, 2002, Yoshiharu Kaneo, p. 22, Hirokawa Publishing Co. More preferable dosage forms of the pharmaceutical solid preparation are pellets, capsules, and pellet-containing tablets. Dosage forms of capsules or pellet-containing tablets are advantageous because the pharmaceutical solid preparation is easier to handle and take. Additionally, from the standpoint of improving tablet strength and humidity measures, the pellet-containing tablet may be coated with a film without impairing the effects of the invention.

When the pharmaceutical solid preparation of the invention takes the form of powders or pellets, the grain size of the powders and pellets is preferably 0.3 to 3 mm, from the viewpoint of production suitability of extrusion.

When the pharmaceutical solid preparation of the invention takes the form of capsules, the size of the capsules is preferably No. 5 to 00, from the viewpoint of ease of handling and taking the preparation.

When the pharmaceutical solid preparation of the invention takes the form of a pellet-containing tablet, the tablet preferably takes the form of a round or couplet, and the diameter or major axis of the tablet is preferably in the range of 6 to 30 mm, from the viewpoint of productivity and ease of handling and taking the preparation.

Production Method of the Pharmaceutical Solid Preparation of the Present Invention The method of producing the pharmaceutical solid preparations of the present invention, particularly the method of producing powders, pellets, and capsules, is described below, but is not limited thereto.

The pharmaceutical solid preparation of the present invention may be produced by various production methods. When producing powders, pellets, and capsules, which are preferable dosage forms in the invention, the production method preferably includes at least an extrusion process. In addition to the extrusion process, the production method preferably includes a wet-kneading process and a spheronization process.

The pharmaceutical solid preparation of the invention is preferably produced through a wet-kneading process, an extrusion process, a spheronization process, a drying process, and optionally a sieving process. In the invention, these processes are preferably carried out in the order of wet-kneading, extrusion, spheronization, and drying.

When the pharmaceutical solid preparation of the invention takes the form of a capsule, the sieving process is further followed by a glidant-mixing process and a capsule-filling process.

When the pharmaceutical solid preparation of the invention takes the form of a pellet-containing tablet, the sieving process is followed by processes of mixing the pellets with suitable additives, lubrication, and tableting. Moreover, film coating may be carried out after the tableting, if needed.

Wet-Kneading Process

The wet-kneading process is the process of wet-kneading the above components with other components such as a binder to allow water to wet each component. At this time, the sugar and/or the sugar alcohol of component (b) may be used in powder form or in the form of a solution in which they are dissolved in water in advance.

Wet-kneading is processed mainly based on a wet high-shearing granulation method. Examples of the machines used in the wet-kneading process include the "New Speed Kneader" (Okada Seiko Co., Ltd.), "Vertical Granulator" (Powrex Corp.), "High Speed Mixer" (Fukae Powtec Co., Ltd.), "High Speed Mixing-Type Mixer/Granulator NMG" (Nara Machinery Co., Ltd.), "Diosna Mixer Granulator" (Mutual Corporation), "Aeromatic-Fielder" (Spectrium), etc.

Extrusion Process

The extrusion process is the process of extruding the wet-kneaded mixture obtained in the wet-kneading process toward a screen to produce cylindrical fibers. Machines for extrusion are not limited, and may be of any type, such as, for example, a screw supply type, a gravity supply type, or a piston supply type. Examples of the screw-type extruder include the "Dome Gran DG-L1", "Twin-Dome Gran TDG-80" and "Twin Dome Gran TDG-110", (Fuji Paudal Co., Ltd.), etc. Examples of the gravity supply-type extruder include the gear roll-type "Gear Pelletizer GCS" (Hosokawa Micron Corp.), radiation-type "FG type Cylindrical Extruder" (Fukae Powtec Co., Ltd.), etc.

When producing powders, the pore size of the screen may be set at 0.3 to 0.5 mm. When producing pellets and capsules, the pore size of the screen may be set at 0.3 to 3 mm.

Spheronization Process

The spheronization process is the process of cutting the cylindrical fibers obtained in the extrusion process into appropriate-sized pieces, and spheronizing them to arrange the form. Examples of machines used in the spheronization process include the "New Speed Kneader" (Okada Seiko Co., Ltd.), the "Marumerizer QJ" (Fuji Paudal. Co., Ltd.), the "CF Granulator" and the "Granurex GX" (Freund Co., Ltd.), etc.

Drying Process

The drying process is the process of drying the particles processed in the spheronization process to remove moisture. Drying may be performed by direct heating or indirect heating. As direct heating, for example, a tray oven, a fluidized-bed dryer, etc. can be employed. As indirect heating, for example, a vacuum dryer, a microwave dryer, a far-infrared dryer, etc. can be employed. Specific examples of the machines used in the drying process include the "Glatt Fluid Bed Granulator WST" and the "Multiplex" (Powrex Corporation), the "Box Aeration Parallel Flow Dryer" and the "Midget Dryer" (Fuji Paudal Co., Ltd.), the "Slit Flow FBS" (Okawara Mfg. Co., Ltd.), the "Flow Dryer NFOD" (Freund Corporation), the "Vibration Dryer" (Chuo Kakohki Co., Ltd.), the "SPHH-200" (Tabai Espec Corp.), etc.

Sieving Process

The sieving process is the process of taking out particles of a fixed grain size from the dry particles. For example, a sieving method is applicable to this process.

Glidant-Mixing Process

The glidant-mixing process is the process of adding a glidant to the particles after the sieving process and mixing the particles and the glidant homogeneously. For example, a diffusion-mixing method (a container-rotating method) is suitable for the glidant-mixing process.

Capsule-filling Process

The capsule-filling process is the process of filling capsules with the particles containing a glidant. Examples of the machines used in the capsule-filling process include the "LIQFIL super" series (Qualicaps Co., Ltd.), the "GKF" series (Bosch Packaging Technology), the "ZANASI" and "MATIC" series (IMA), etc.

Effect of the Invention

In the present invention, the use of sugar and/or sugar alcohol that have a specific property can provide appropriate plasticity to a kneaded mixture with a high methacrylic acid-based enteric polymer content. Therefore, it is not necessary to add a plasticizer to the pharmaceutical solid preparation of the present invention, and it is thus free from the following drawbacks caused by adding a plasticizer: the combination of a plasticizer promotes metamorphosis and deformation of the methacrylic acid-based enteric polymer, making it easy to form films composed of the enteric polymer on the inside a screen. Such films can cause obstruction of the screen and the failure of the extruder. Furthermore, the plasticizer remaining in the solid preparation promotes the metamorphosis and deformation of the methacrylic acid-based enteric polymer with time. As a result, the dissolution change of the drug with time is unavoidable.

Since the pharmaceutical solid preparation of the invention can contain a large amount of methacrylic acid-based enteric polymer without the use of a plasticizer, the preparation has high-level release controllability that suppresses drug release in the upper gastrointestinal tract and rapidly releases the drug in the lower gastrointestinal tract.

The pharmaceutical solid preparation of the invention contains methacrylic acid-based enteric polymers with good pH response, and thereby has high-level release controllability. Accordingly, there is no need for a coating process that is conducted in the production of enteric preparations, time dependent-type preparations, colon-specific release-type preparations, or the like. For this reason, according to the present invention, pharmaceutical solid preparations having desired sustained release properties can be produced inexpensively and very productively.

BEST MODE FOR CARRYING OUT THE INVENTION

EXAMPLES

Figure 1:
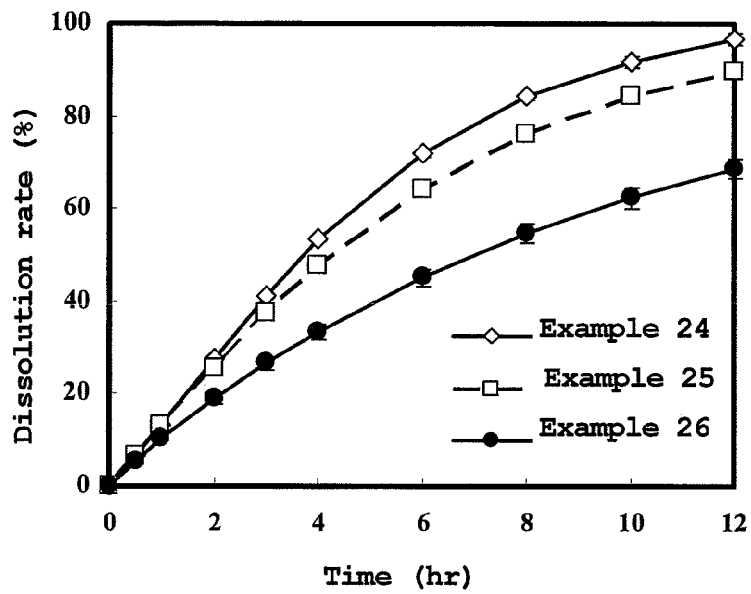
FIG. 1 shows dissolution test results of Examples 24, 25, and 26.

The present invention will be explained in more detail below with reference to Examples and Comparative Examples.

Example 1

Cilostazol (100 g), 15 g of Sunmalt-S (maltose monohydrate; Sanwa Cornstarch Co., Ltd.), 30 g of Eudragit 5100 (methacrylic acid copolymer S; Degussa AG), and 10 g of Ceolus PH-301 (crystalline cellulose; Asahi Kasei Chemicals Corp.) were fed into a Speed Kneader NSK-150 (a mixing granulator; Okada Seiko Co., Ltd.). Then, 20 g of 5 w/v % HPC-L aqueous solution (hydroxypropylcellulose; Nippon Soda Co., Ltd.) and 10 g of purified water were added as binder solutions and wet-kneaded for 180 seconds. The kneaded product was gradually fed into a Dome Gran DG-L1 (an extruder; Fuji Paudal Co., Ltd.) equipped with a dome-shaped die having a pore size of 0.6 mm and an aperture ratio of 22.6%. Extrusion was repeated three times at a screw speed of 40 rpm to produce fine noodle-like extrudates about 2 to 3 cm in length. Using a Marumerizer QJ-400 (a spheronizer; Fuji Paudal Co., Ltd.) equipped with a cross-hatch plate in which pitches are carved at intervals of 3 mm, the extrudates were processed for 20 seconds at a rotation speed of about 1000 rpm, producing wet pellets. The wet pellets were dried with an SPHH-200 (a tray oven; Tabai Espec Corp.) set at 70° C., for 2 to 3 hours to obtain dry pellets.

The fine noodle-like extrudates obtained in the foregoing extrusion process greatly affect the quality and productivity of the pharmaceutical solid preparation of the present invention. On a small-amount scale, since the amount of kneaded product passed through a screen is small, the pressure applied to the kneaded product is low through one passing, and productivity is difficult to estimate. Accordingly, when productivity is estimated based on a small amount of kneaded product, one kneaded product is repeatedly passed through a screen several times, and the condition of solid compositions accumulated in the gap between the screen and screw is stabilized. In such a condition, productivity is preferably recognized. In the following examples, one kneaded product was subjected to extrusion three times, and the temperature of the kneaded product was measured after each extrusion. The plasticity of the kneaded product was checked from these temperatures.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 1

| Wet-Kneaded Product | Measured Temperature |
|---|---|
| After Wet-Kneading | 24.2° C. |
| After 1$^{st}$ Extrusion | 31.3° C. |
| After 2$^{nd}$ Extrusion | 33.0° C. |
| After 3$^{rd}$ Extrusion | 33.0° C. |
| Temperature Difference Before and After 1$^{st}$ Extrusion | Δ 7.1° C. |

These results show that mixing maltose monohydrate can impart moderate plasticity to a wet-kneaded product containing a large amount of methacrylic acid copolymer S.

Example 2

Cilostazol (100 g), 15 g of Erythritol 100M (erythritol; Nikken Chemicals Co., Ltd.), 30 g of Eudragit 5100 (methacrylic acid copolymer S; Degussa AG), and 10 g of Ceolus PH-301 (crystalline cellulose; Asahi Kasei Chemicals Corp.) were fed into a Speed Kneader NSK-150 (a mixing granulator; Okada Seiko Co., Ltd.). Then, 20 g of 5 w/v % HPC-L aqueous solution (hydroxypropylcellulose; Nippon Soda Co., Ltd.) and 8.5 g of purified water were added as binder solutions and wet-kneaded for 160 seconds. The kneaded product was gradually fed into a Dome Gran DG-L1 (an extruder; Fuji Paudal Co., Ltd.) equipped with a dome-shaped die having a pore size of 0.6 mm and an aperture ratio of 19.3%. Extrusion was repeated three times at a screw speed of 40 rpm to produce fine noodle-like extrudates about 2 to 3 cm in length. Using a Marumerizer QJ-400 (a spheronizer; Fuji Paudal Co., Ltd.) equipped with a cross-hatch plate in which pitches are carved at intervals of 3 mm, the extrudates were processed for 15 seconds at a rotation speed of about 1000 rpm, producing wet pellets. The wet pellets were dried with an SPHH-200 (a tray oven; Tabai Espec Corp.) set at 70° C., for 2 to 3 hours to obtain dry pellets.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 2

| Wet-Kneaded Product | Measured Temperature |
|---|---|
| After Wet-Kneading | 24.3° C. |
| After 1$^{st}$ Extrusion | 31.2° C. |
| After 2$^{nd}$ Extrusion | 33.6° C. |
| After 3$^{rd}$ Extrusion | 34.6° C. |
| Temperature Difference Before and After 1$^{st}$ Extrusion | Δ 6.9° C. |

These results show that mixing erythritol can impart moderate plasticity to a wet-kneaded product containing a large amount of methacrylic acid copolymer S.

Example 3

Cilostazol (100 g), 15 g of Sorbitol SP (sorbitol; Nikken Fine Chemicals Co., Ltd.), 30 g of Eudragit 5100 (methacrylic acid copolymer S; Degussa AG), and 10 g of Ceolus PH-301 (crystalline cellulose; Asahi Kasei Chemicals Corp.) were fed into a Speed Kneader NSK-150 (a mixing granulator; Okada Seiko Co., Ltd.). Then, 20 g of 5 w/v % HPC-L aqueous solution (hydroxypropylcellulose; Nippon Soda Co., Ltd.) and 8 g of purified water were added as binder solutions and wet-kneaded for 90 seconds. The kneaded product was gradually fed into a Dome Gran DG-L1 (an extruder; Fuji Paudal Co., Ltd.) equipped with a dome-shaped die having a pore size of 0.6 mm and an aperture ratio of 22.6%. Extrusion was repeated three times at a screw speed of 40 rpm to produce fine noodle-like extrudates about 2 to 3 cm in length. Using a Marumerizer QJ-400 (a spheronizer; Fuji Paudal Co., Ltd.) equipped with a cross-hatch plate in which pitches are carved at intervals of 3 mm, the extrudates were processed for 20 seconds at a rotation speed of about 1000 rpm, producing wet pellets. The wet pellets were dried with an SPHH-200 (a tray oven; Tabai Espec Corp.) set at 70° C., for 2 to 3 hours to obtain dry pellets.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 3

| Wet-Kneaded Product | Measured Temperature |
| --- | --- |
| After Wet-Kneading | 24.4° C. |
| After 1$^{st}$ Extrusion | 30.3° C. |
| After 2$^{nd}$ Extrusion | 34.6° C. |
| After 3$^{rd}$ Extrusion | 38.0° C. |
| Temperature Difference Before and After 1$^{st}$ Extrusion | Δ 5.9° C. |

These results show that mixing sorbitol can impart moderate plasticity to a wet-kneaded product containing a large amount of methacrylic acid copolymer S.

Example 4

Cilostazol (100 g), 15 g of Lactitol LC-1 (lactitol monohydrate; Nikken Fine Chemicals Co., Ltd.), 30 g of Eudragit S100 (methacrylic acid copolymer S; Degussa AG), and 10 g of Ceolus PH-301 (crystalline cellulose; Asahi Kasei Chemicals Corp.) were fed into a Speed Kneader NSK-150 (a mixing granulator; Okada Seiko Co., Ltd.). Then, 20 g of 5 w/v % HPC-L aqueous solution (hydroxypropylcellulose; Nippon Soda Co., Ltd.) and 8.5 g of purified water were added as binder solutions and wet-kneaded for 170 seconds. The kneaded product was gradually fed into a Dome Gran DG-L1 (an extruder; Fuji Paudal Co., Ltd.) equipped with a dome-shaped die having a pore size of 0.6 mm and an aperture ratio of 19.3%. Extrusion was repeated three times at a screw speed of 40 rpm to produce fine noodle-like extrudates about 2 to 3 cm in length. Using a Marumerizer QJ-400 (a spheronizer; Fuji Paudal Co., Ltd.) equipped with a cross-hatch plate in which pitches are carved at intervals of 3 mm, the extrudates were processed for 25 seconds at a rotation speed of about 1000 rpm, producing wet pellets. The wet pellets were dried with an SPHH-200 (a tray oven; Tabai Espec Corp.) set at 70° C., for 2 to 3 hours to obtain dry pellets.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 4

| Wet-Kneaded Product | Measured Temperature |
| --- | --- |
| After Wet-Kneading | 23.6° C. |
| After 1$^{st}$ Extrusion | 31.6° C. |
| After 2$^{nd}$ Extrusion | 34.6° C. |
| After 3$^{rd}$ Extrusion | 38.2° C. |
| Temperature Difference Before and After 1$^{st}$ Extrusion | Δ 8.0° C. |

These results show that mixing lactitol monohydrate can impart moderate plasticity to a wet-kneaded product containing a large amount of methacrylic acid copolymer S.

Example 5

Cilostazol (100 g), 15 g of Trehalose P (trehalose dihydrate; Hayashibara Biochemical Laboratories, Inc.), 30 g of Eudragit S100 (methacrylic acid copolymer S; Degussa AG), and 10 g of Ceolus PH-301 (crystalline cellulose; Asahi Kasei Chemicals Corp.) were fed into a Speed Kneader NSK-150 (a mixing granulator; Okada Seiko Co., Ltd.). Then, 20 g of 5 w/v % HPC-L aqueous solution (hydroxypropylcellulose; Nippon Soda Co., Ltd.) and 8.5 g of purified water were added as binder solutions and wet-kneaded for 140 seconds. The kneaded product was gradually fed into a Dome Gran DG-L1 (an extruder; Fuji Paudal Co., Ltd.) equipped with a dome-shaped die having a pore size of 0.6 mm and an aperture ratio of 19.3%. Extrusion was repeated three times at a screw speed of 40 rpm to produce fine noodle-like extrudates about 2 to 3 cm in length. Using a Marumerizer QJ-400 (a spheronizer; Fuji Paudal Co., Ltd.) equipped with a cross-hatch plate in which pitches are carved at intervals of 3 mm, the extrudates were processed for 30 seconds at a rotation speed of about 1000 rpm, producing wet pellets. The wet pellets were dried with an SPHH-200 (a tray oven; Tabai Espec Corp.) set at 70° C., for 2 to 3 hours to obtain dry pellets.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 5

| Wet-Kneaded Product | Measured Temperature |
| --- | --- |
| After Wet-Kneading | 23.1° C. |
| After 1$^{st}$ Extrusion | 32.8° C. |
| After 2$^{nd}$ Extrusion | 37.8° C. |
| After 3$^{rd}$ Extrusion | 43.2° C. |
| Temperature Difference Before and After 1$^{st}$ Extrusion | Δ 9.7° C. |

These results show that mixing trehalose dihydrate can impart moderate plasticity to a wet-kneaded product containing a large amount of methacrylic acid copolymer S.

Example 6

Cilostazol (100 g), 15 g of Xylitol P (xylitol; Nikken Chemical Co., Ltd.), 30 g of Eudragit S100 (methacrylic acid copolymer S; Degussa AG), and 10 g of Ceolus PH-301 (crystalline cellulose; Asahi Kasei Chemicals Corp.) were fed into a Speed Kneader NSK-150 (a mixing granulator; Okada Seiko Co., Ltd.). Then, 20 g of 5 w/v % HPC-L aqueous solution (hydroxypropylcellulose; Nippon Soda Co., Ltd.) and 8.5 g of purified water were added as binder solutions and wet-kneaded for 115 seconds. The kneaded product was gradually fed into a Dome Gran DG-L1 (an extruder; Fuji Paudal Co., Ltd.) equipped with a dome-shaped die having a pore size of 0.6 mm and an aperture ratio of 19.3%. Extrusion was repeated three times at a screw speed of 40 rpm to produce fine noodle-like extrudates about 2 to 3 cm in length. Using a Marumerizer QJ-400 (a spheronizer; Fuji Paudal Co., Ltd.) equipped with a cross-hatch plate in which pitches are carved at intervals of 3 mm, the extrudates were processed for 25 seconds at a rotation speed of about 1000 rpm, producing wet pellets. The wet pellets were dried with an SPHH-200 (a tray oven; Tabai Espec Corp.) set at 70° C., for 2 to 3 hours to obtain dry pellets.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 6

| Wet-Kneaded Product | Measured Temperature |
| --- | --- |
| After Wet-Kneading | 23.1° C. |
| After 1$^{st}$ Extrusion | 31.3° C. |
| After 2$^{nd}$ Extrusion | 33.3° C. |
| After 3$^{rd}$ Extrusion | 37.6° C. |
| Temperature Difference Before and After 1$^{st}$ Extrusion | Δ 8.2° C. |

These results show that mixing xylitol can impart moderate plasticity to a wet-kneaded product containing a large amount of methacrylic acid copolymer S.

Comparative Example 1

Cilostazol (100 g), 15 g of Wyndale Lactose 200M (lactose monohydrate; The Lactose Company of New Zealand Limited), 30 g of Eudragit 5100 (methacrylic acid copolymer S; Degussa AG), and 10 g of Ceolus PH-301 (crystalline cellulose; Asahi Kasei Chemicals Corp.) were fed into a Speed Kneader NSK-150 (a mixing granulator; Okada Seiko Co., Ltd.). Then, 20 g of 5 w/v % HPC-L aqueous solution (hydroxypropylcellulose; Nippon Soda Co., Ltd.) and 10 g of purified water were added as binder solutions and wet-kneaded for 240 seconds. The kneaded product was gradually fed into a Dome Gran DG-L1 (an extruder; Fuji Paudal Co., Ltd.) equipped with a dome-shaped die having a pore size of 0.6 mm and an aperture ratio of 22.6%. Extrusion was repeated two times at a screw speed of 40 rpm; however, the third extrusion was stopped because a large load was imposed on the DG-L1 and the current value of the motor changed significantly.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 7

| Wet-Kneaded Product | Measured Temperature |
| --- | --- |
| After Wet-Kneading | 23.5° C. |
| After 1$^{st}$ Extrusion | 51.7° C. |
| After 2$^{nd}$ Extrusion | 56.0° C. |

TABLE 7-continued

| Wet-Kneaded Product | Measured Temperature |
| --- | --- |
| After 3$^{rd}$ Extrusion | Not Extruded |
| Temperature Difference Before and After 1$^{st}$ Extrusion | Δ 28.2° C. |

These results show that mixing lactose monohydrate fails to impart moderate plasticity to a wet-kneaded product containing a large amount of methacrylic acid copolymer S.

Comparative Example 2

Cilostazol (100 g), 15 g of Pearlitol 50C (D-mannitol; Roquette), 30 g of Eudragit 5100 (methacrylic acid copolymer S; Degussa AG), and 10 g of Ceolus PH-301 (crystalline cellulose; Asahi Kasei Chemicals Corp.) were fed into a Speed Kneader NSK-150 (a mixing granulator; Okada Seiko Co., Ltd.). Then, 20 g of 5 w/v % HPC-L aqueous solution (hydroxypropylcellulose; Nippon Soda Co., Ltd.) and 10 g of purified water were added as binder solutions and wet-kneaded for 300 seconds. The kneaded product was gradually fed into a Dome Gran DG-L1 (an extruder; Fuji Paudal Co., Ltd.) equipped with a dome-shaped die having a pore size of 0.6 mm and an aperture ratio of 19.3%. Extrusion was repeated two times at a screw speed of 40 rpm; however, the third extrusion was stopped because a large load was imposed on the DG-L1 and the current value of the motor changed significantly.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 8

| Wet-Kneaded Product | Measured Temperature |
| --- | --- |
| After Wet-Kneading | 24.3° C. |
| After 1$^{st}$ Extrusion | 42.7° C. |
| After 2$^{nd}$ Extrusion | 53.2° C. |
| After 3$^{rd}$ Extrusion | Not Extruded |
| Temperature Difference Before and After 1$^{st}$ Extrusion | Δ 18.4° C. |

These results show that mixing D-mannitol fails to impart moderate plasticity to a wet-kneaded product containing a large amount of methacrylic acid copolymer S.

Example 7

Cilostazol (100 g), 25 g of Sunmalt-S (maltose monohydrate; Sanwa Cornstarch Co., Ltd.), 60 g of Eudragit 5100 (methacrylic acid copolymer S; Degussa AG), and 20 g of Ceolus PH-301 (crystalline cellulose; Asahi Kasei Chemicals Corp.) were fed into a Speed Kneader NSK-150 (a mixing granulator; Okada Seiko Co., Ltd.). Then, 30 g of 5 w/v % HPC-L aqueous solution (hydroxypropylcellulose; Nippon Soda Co., Ltd.) and 18 g of purified water were added as binder solutions and wet-kneaded for 320 seconds. The kneaded product was gradually fed into a Dome Gran DG-L1 (an extruder; Fuji Paudal Co., Ltd.) equipped with a dome-shaped die having a pore size of 0.6 mm and an aperture ratio of 22.6%. Extrusion was repeated three times at a screw speed of 40 rpm to produce fine noodle-like extrudates about 2 to 3 cm in length. Using a Marumerizer QJ-400 (a spheronizer; Fuji Paudal Co., Ltd.) equipped with a cross-hatch plate in which pitches are carved at intervals of 3 mm, the extrudates were processed for 20 seconds at a rotation speed of about 1000 rpm, producing wet pellets. The wet pellets were dried with an SPHH-200 (a tray oven; Tabai Espec Corp.) set at 70° C., for 2 to 3 hours to obtain dry pellets.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 9

| Wet-Kneaded Product | Measured Temperature |
| --- | --- |
| After Wet-Kneading | 25.6° C. |
| After 1$^{st}$ Extrusion | 30.3° C. |
| After 2$^{nd}$ Extrusion | 32.5° C. |
| After 3$^{rd}$ Extrusion | 34.7° C. |
| Temperature Difference Before and After 1$^{st}$ Extrusion | Δ 4.7° C. |

These results show that mixing maltose monohydrate can impart moderate plasticity to a wet-kneaded product containing a large amount of methacrylic acid copolymer S.

Example 8

Cilostazol (100 g), 25 g of Erythritol 100M (erythritol; Nikken Chemicals Co., Ltd.), 60 g of Eudragit S100 (methacrylic acid copolymer S; Degussa AG), and 20 g of Ceolus PH-301 (crystalline cellulose; Asahi Kasei Chemicals Corp.) were fed into a Speed Kneader NSK-150 (a mixing granulator; Okada Seiko Co., Ltd.). Then, 30 g of 5 w/v % HPC-L aqueous solution (hydroxypropylcellulose; Nippon Soda Co., Ltd.) and 15 g of purified water were added as biunder solutions and wet-kneaded for 100 seconds. The kneaded product was gradually fed into a Dome Gran DG-L1 (an extruder; Fuji Paudal Co., Ltd.) equipped with a dome-shaped die having a pore size of 0.6 mm and an aperture ratio of 19.3%. Extrusion was repeated three times at a screw speed of 40 rpm to produce fine noodle-like extrudates about 2 to 3 cm in length. Using a Marumerizer QJ-400 (a spheronizer; Fuji Paudal Co., Ltd.) equipped with a cross-hatch plate in which pitches are carved at intervals of 3 mm, the extrudates were processed for 30 seconds at a rotation speed of about 1000 rpm, producing wet pellets. The wet pellets were dried with an SPHH-200 (a tray oven; Tabai Espec Corp.) set at 70° C., for 2 to 3 hours to obtain dry pellets.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 10

| Wet-Kneaded Product | Measured Temperature |
| --- | --- |
| After Wet-Kneading | 22.9° C. |
| After 1$^{st}$ Extrusion | 32.6° C. |
| After 2$^{nd}$ Extrusion | 34.3° C. |
| After 3$^{rd}$ Extrusion | 38.7° C. |
| Temperature Difference Before and After 1$^{st}$ Extrusion | Δ 9.7° C. |

These results show that mixing erythritol can impart moderate plasticity to a wet-kneaded product containing a large amount of methacrylic acid copolymer S.

Example 9

Cilostazol (100 g), 25 g of Lactitol LC-1 (lactitol monohydrate; Nikken Fine Chemicals Co., Ltd.), 60 g of Eudragit S100 (methacrylic acid copolymer S; Degussa AG), and 20 g of Ceolus PH-301 (crystalline cellulose; Asahi Kasei Chemicals Corp.) were fed into a Speed Kneader NSK-150 (a mixing granulator; Okada Seiko Co., Ltd.). Then, 30 g of 5 w/v % HPC-L aqueous solution (hydroxypropylcellulose; Nippon Soda Co., Ltd.) and 16.5 g of purified water were added as binder solutions and wet-kneaded for 140 seconds. The kneaded product was gradually fed into a Dome Gran DG-L1 (an extruder; Fuji Paudal Co., Ltd.) equipped with a dome-shaped die having a pore size of 0.6 mm and an aperture ratio of 19.3%. Extrusion was repeated three times at a screw speed of 40 rpm to produce fine noodle-like extrudates about 2 to 3 cm in length. Using a Marumerizer QJ-400 (a spheronizer; Fuji Paudal Co., Ltd.) equipped with a cross-hatch plate in which pitches are carved at intervals of 3 mm, the extrudates were processed for 30 seconds at a rotation speed of about 1000 rpm, producing wet pellets. The wet pellets were dried with an SPHH-200 (a tray oven; Tabai Espec Corp.) set at 70° C., for 2 to 3 hours to obtain dry pellets.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 11

| Wet-Kneaded Product | Measured Temperature |
| --- | --- |
| After Wet-Kneading | 25.0° C. |
| After 1$^{st}$ Extrusion | 31.0° C. |
| After 2$^{nd}$ Extrusion | 36.5° C. |
| After 3$^{rd}$ Extrusion | 39.5° C. |
| Temperature Difference Before and After 1$^{st}$ Extrusion | Δ 6.0° C. |

These results show that mixing lactitol monohydrate can impart moderate plasticity to a wet-kneaded product containing a large amount of methacrylic acid copolymer S.

Example 10

Cilostazol (100 g), 25 g of Sorbitol SP (sorbitol; Nikken Fine Chemicals Co., Ltd.), 60 g of Eudragit S100 (methacrylic acid copolymer S; Degussa AG), and 20 g of Ceolus PH-301 (crystalline cellulose; Asahi Kasei Chemicals Corp.) were fed into a Speed Kneader NSK-150 (a mixing granulator; Okada Seiko Co., Ltd.). Then, 30 g of 5 w/v % HPC-L aqueous solution (hydroxypropylcellulose; Nippon Soda Co., Ltd.) and 15 g of purified water were added as binder solutions and wet-kneaded for 50 seconds. The kneaded product was gradually fed into a Dome Gran DG-L1 (an extruder; Fuji Paudal Co., Ltd.) equipped with a dome-shaped die having a pore size of 0.6 mm and an aperture ratio of 22.6%. Extrusion was repeated three times at a screw speed of 40 rpm to produce fine noodle-like extrudates about 2 to 3 cm in length. Using a Marumerizer QJ-400 (a spheronizer; Fuji Paudal Co., Ltd.) equipped with a cross-hatch plate in which pitches are carved at intervals of 3 mm, the extrudates were processed for 25 seconds at a rotation speed of about 1000 rpm, producing wet pellets. The wet pellets were dried with an SPHH-200 (a tray oven; Tabai Espec Corp.) set at 70° C., for 2 to 3 hours to obtain dry pellets.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 12

| Wet-Kneaded Product | Measured Temperature |
|---|---|
| After Wet-Kneading | 22.5° C. |
| After 1$^{st}$ Extrusion | 33.0° C. |
| After 2$^{nd}$ Extrusion | 33.5° C. |
| After 3$^{rd}$ Extrusion | 35.0° C. |
| Temperature Difference Before and After 1$^{st}$ Extrusion | Δ 10.5° C. |

These results show that mixing sorbitol can impart moderate plasticity to a wet-kneaded product containing a large amount of methacrylic acid copolymer S.

Example 11

Cilostazol (100 g), 25 g of Trehalose P (trehalose dihydrate; Hayashibara Biochemical Laboratories, Inc.), 60 g of Eudragit S100 (methacrylic acid copolymer S; Degussa AG), and 20 g of Ceolus PH-301 (crystalline cellulose; Asahi Kasei Chemicals Corp.) were fed into a Speed Kneader NSK-150 (a mixing granulator; Okada Seiko Co., Ltd.). Then, 30 g of 5 w/v % HPC-L aqueous solution (hydroxypropylcellulose; Nippon Soda Co., Ltd.) and 16.5 g of purified water were added as binder solutions and wet-kneaded for 110 seconds. The kneaded product was gradually fed into a Dome Gran DG-L1 (an extruder; Fuji Paudal Co., Ltd.) equipped with a dome-shaped die having a pore size of 0.6 mm and an aperture ratio of 19.3%. Extrusion was repeated three times at a screw speed of 40 rpm to produce fine noodle-like extrudates about 2 to 3 cm in length. Using a Marumerizer QJ-400 (a spheronizer; Fuji Paudal Co., Ltd.) equipped with a cross-hatch plate in which pitches are carved at intervals of 3 mm, the extrudates were processed for 30 seconds at a rotation speed of about 1000 rpm, producing wet pellets. The wet pellets were dried with an SPHH-200 (a tray oven; Tabai Espec Corp.) set at 70° C., for 2 to 3 hours to obtain dry pellets.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 13

| Wet-Kneaded Product | Measured Temperature |
|---|---|
| After Wet-Kneading | 23.8° C. |
| After 1$^{st}$ Extrusion | 32.5° C. |
| After 2$^{nd}$ Extrusion | 34.8° C. |
| After 3$^{rd}$ Extrusion | 36.8° C. |
| Temperature Difference Before and After 1$^{st}$ Extrusion | Δ 8.7° C. |

These results show that mixing trehalose dihydrate can impart moderate plasticity to a wet-kneaded product containing a large amount of methacrylic acid copolymer S.

Example 12

Cilostazol (100 g), 25 g of Xylitol P (xylitol; Nikken Fine Chemicals Co., Ltd.), 60 g of Eudragit S100 (methacrylic acid copolymer S; Degussa AG), and 20 g of Ceolus PH-301 (crystalline cellulose; Asahi Kasei Chemicals Corp.) were fed into a Speed Kneader NSK-150 (a mixing granulator; Okada Seiko Co., Ltd.). Then, 30 g of 5 w/v % HPC-L aqueous solution (hydroxypropylcellulose; Nippon Soda Co., Ltd.) and 15 g of purified water were added as binder solutions and wet-kneaded for 50 seconds. The kneaded product was gradually fed into a Dome Gran DG-L1 (an extruder; Fuji Paudal Co., Ltd.) equipped with a dome-shaped die having a pore size of 0.6 mm and an aperture ratio of 22.6%. Extrusion was repeated three times at a screw speed of 40 rpm to produce fine noodle-like extrudates about 2 to 3 cm in length. Using a Marumerizer QJ-400 (a spheronizer; Fuji Paudal Co., Ltd.) equipped with a cross-hatch plate in which pitches are carved at intervals of 3 mm, the extrudates were processed for 20 seconds at a rotation speed of about 1000 rpm, producing wet pellets. The wet pellets were dried with an SPHH-200 (a tray oven; Tabai Espec Corp.) set at 70° C., for 2 to 3 hours to obtain dry pellets.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 14

| Wet-Kneaded Product | Measured Temperature |
|---|---|
| After Wet-Kneading | 22.2° C. |
| After 1$^{st}$ Extrusion | 29.3° C. |
| After 2$^{nd}$ Extrusion | 30.5° C. |
| After 3$^{rd}$ Extrusion | 31.6° C. |
| Temperature Difference Before and After 1$^{st}$ Extrusion | Δ 7.3° C. |

These results show that mixing xylitol can impart moderate plasticity to a wet-kneaded product containing a large amount of methacrylic acid copolymer S.

Comparative Example 3

Cilostazol (100 g), 25 g of sucrose micronized by a hammer mill (granulated sugar CH; Ensuiko Sugar Refining Co., Ltd.), 60 g of Eudragit S100 (methacrylic acid copolymer S; Degussa AG), and 20 g of Ceolus PH-301 (crystalline cellulose; Asahi Kasei Chemicals Corp.) were fed into a Speed Kneader NSK-150 (a mixing granulator; Okada Seiko Co., Ltd.). Then, 30 g of 5 w/v % HPC-L aqueous solution (hydroxypropylcellulose; Nippon Soda Co., Ltd.) and 17 g of purified water were added as binder solutions and wet-kneaded for 90 seconds. The kneaded product was gradually fed into a Dome Gran DG-L1 (an extruder; Fuji Paudal Co., Ltd.) equipped with a dome-shaped die having a pore size of 0.6 mm and an aperture ratio of 19.3%. Extrusion was repeated two times at a screw speed of 40 rpm; however, the third extrusion was stopped because a large load was imposed on the DG-L1 and the current value of the motor changed significantly.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 15

| Wet-Kneaded Product | Measured Temperature |
| --- | --- |
| After Wet-Kneading | 23.6° C. |
| After 1$^{st}$ Extrusion | 42.7° C. |
| After 2$^{nd}$ Extrusion | 50.3° C. |
| After 3$^{rd}$ Extrusion | 55.2° C. (Suspended) |
| Temperature Difference Before and After 1$^{st}$ Extrusion | Δ 19.1° C. |

These results show that mixing sucrose fails to impart moderate plasticity to a wet-kneaded product containing a large amount of methacrylic acid copolymer S.

Reference Example 1

Amorphous tolvaptan was prepared in the following manner: 7-chloro-5-hydroxy-1-[2-methyl-4-(2-methyl benzoylamino) benzoyl]-2,3,4,5-tetrahydro-1H-benzoazepine (100 g) and 50 g of hydroxypropylcellulose (HPC-SL, hydroxypropoxyl-group content: 53 to 78 wt. %; Nippon Soda Co., Ltd.) were dissolved in a mixed solution of dichloromethane (1390 g) and ethanol (350 g). The solution was processed with a spray dryer (Type ODT-8; Ohkawara Kakohki Co., Ltd.), and then dried immediately with a vacuum dryer (LCV-232; Tabai Espec Corp.) to prepare an amorphous powder (amorphous tolvaptan).

Example 13

The amorphous tolvaptan (90 g; tolvaptan amount: 60 g) prepared in Reference Example 1, 15 g of Sunmalt-S (maltose monohydrate; Sanwa Cornstarch Co., Ltd.), 30 g of Eudragit S100 (methacrylic acid copolymer S; Degussa AG), and 10 g of Ceolus PH-301 (crystalline cellulose; Asahi Kasei Chemicals Corp.) were fed into a Speed Kneader NSK-150 (a mixing granulator; Okada Seiko Co., Ltd.). Then, 20 g of 5 w/v % HPC-L aqueous solution (hydroxypropylcellulose; Nippon Soda Co., Ltd.) and 15 g of purified water were added as binder solutions and wet-kneaded for 110 seconds. The kneaded product was gradually fed into a Dome Gran DG-L1 (an extruder; Fuji Paudal Co., Ltd.) equipped with a dome-shaped die having a pore size of 0.6 mm and an aperture ratio of 22.6%. Extrusion was repeated three times at a screw speed of 40 rpm to produce fine noodle-like extrudates about 2 to 3 cm in length. Using a Marumerizer QJ-400 (a spheronizer; Fuji Paudal Co., Ltd.) equipped with a cross-hatch plate in which pitches are carved at intervals of 3 mm, the extrudates were processed for 25 seconds at a rotation speed of about 1000 rpm, producing wet pellets. The wet pellets were dried with an SPHH-200 (a tray oven; Tabai Espec Corp.) set at 70° C., for 2 to 3 hours to obtain dry pellets.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 16

| Wet-Kneaded Product | Measured Temperature |
| --- | --- |
| After Wet-Kneading | 23.2° C. |
| After 1$^{st}$ Extrusion | 28.0° C. |
| After 2$^{nd}$ Extrusion | 27.7° C. |
| After 3$^{rd}$ Extrusion | 29.5° C. |
| Temperature Difference Before and After 1$^{st}$ Extrusion | Δ 4.8° C. |

These results show that mixing maltose monohydrate can impart moderate plasticity to a wet-kneaded product containing a large amount of methacrylic acid copolymer S.

Example 14

The amorphous tolvaptan (90 g; tolvaptan amount: 60 g) prepared in Reference Example 1, 15 g of Erythritol 100M (erythritol; Nikken Fine Chemicals Co., Ltd.), 30 g of Eudragit S100 (methacrylic acid copolymer S; Degussa AG), and 10 g of Ceolus PH-301 (crystalline cellulose; Asahi Kasei Chemicals Corp.) were fed into a Speed Kneader NSK-150 (a mixing granulator; Okada Seiko Co., Ltd.). Then, 20 g of 5 w/v % HPC-L aqueous solution (hydroxypropylcellulose; Nippon Soda Co., Ltd.) and 13 g of purified water were added as binder solutions and wet-kneaded for 90 seconds. The kneaded product was gradually fed into a Dome Gran DG-L1 (an extruder; Fuji Paudal Co., Ltd.) equipped with a dome-shaped die having a pore size of 0.6 mm and an aperture ratio of 19.3%. Extrusion was repeated three times at a screw speed of 40 rpm to produce fine noodle-like extrudates about 2 to 3 cm in length. Using a Marumerizer QJ-400 (a spheronizer; Fuji Paudal Co., Ltd.) equipped with a cross-hatch plate in which pitches are carved at intervals of 3 mm, the extrudates were processed for 20 seconds at a rotation speed of about 1000 rpm, producing wet pellets. The wet pellets were dried with an SPHH-200 (a tray oven; Tabai Espec Corp.) set at 70° C., for 2 to 3 hours to obtain dry pellets.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 17

| Wet-Kneaded Product | Measured Temperature |
| --- | --- |
| After Wet-Kneading | 23.1° C. |
| After 1$^{st}$ Extrusion | 29.5° C. |
| After 2$^{nd}$ Extrusion | 30.4° C. |
| After 3$^{rd}$ Extrusion | 31.8° C. |
| Temperature Difference Before and After 1$^{st}$ Extrusion | Δ 6.4° C. |

These results show that mixing erythritol can impart moderate plasticity to a wet-kneaded product containing a large amount of methacrylic acid copolymer S.

Example 15

The amorphous tolvaptan (90 g; tolvaptan amount: 60 g) prepared in Reference Example 1, 15 g of Lactitol LC-1 (lactitol monohydrate; Nikken Fine Chemicals Co., Ltd.), 30 g of Eudragit S100 (methacrylic acid copolymer S; Degussa AG), and 10 g of Ceolus PH-301 (crystalline cellulose; Asahi Kasei Chemicals Corp.) were fed into a Speed Kneader NSK-150 (a mixing granulator; Okada Seiko Co., Ltd.). Then, 20 g of 5 w/v % HPC-L aqueous solution (hydroxypropylcellulose; Nippon Soda Co., Ltd.) and 13 g of purified water were added as binder solutions and wet-kneaded for 120 seconds. The kneaded product was gradually fed into a Dome Gran DG-L1 (an extruder; Fuji Paudal Co., Ltd.) equipped with a dome-shaped die having a pore size of 0.6 mm and an aperture ratio of 22.6%. Extrusion was repeated three times at a screw speed of 40 rpm to produce fine noodle-like extrudates about 2 to 3 cm in length. Using a Marumerizer QJ-400 (a spheronizer; Fuji Paudal Co., Ltd.) equipped with a cross-hatch plate in which pitches are carved at intervals of 3 mm, the extrudates were processed for 30 seconds at a rotation speed of about 1000 rpm, producing wet pellets. The wet pellets were dried with an SPHH-200 (a tray oven; Tabai Espec Corp.) set at 70° C., for 2 to 3 hours to obtain dry pellets.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 18

| Wet-Kneaded Product | Measured Temperature |
| --- | --- |
| After Wet-Kneading | 24.2° C. |
| After 1$^{st}$ Extrusion | 30.3° C. |
| After 2$^{nd}$ Extrusion | 31.2° C. |
| After 3$^{rd}$ Extrusion | 36.5° C. |
| Temperature Difference Before and After 1$^{st}$ Extrusion | Δ 6.1° C. |

These results show that mixing lactitol monohydrate can impart moderate plasticity to a wet-kneaded product containing a large amount of methacrylic acid copolymer S.

Example 16

The amorphous tolvaptan (90 g; tolvaptan amount: 60 g) prepared in Reference Example 1, 15 g of Trehalose P (trehalose dihydrate; Hayashibara Biochemical Laboratories, Inc.), 30 g of Eudragit S100 (methacrylic acid copolymer S; Degussa AG), and 10 g of Ceolus PH-301 (crystalline cellulose; Asahi Kasei Chemicals Corp.) were fed into a Speed Kneader NSK-150 (a mixing granulator; Okada Seiko Co., Ltd.). Then, 20 g of 5 w/v % HPC-L aqueous solution (hydroxypropylcellulose; Nippon Soda Co., Ltd.) and 14.5 g of purified water were added as binder solutions and wet-kneaded for 130 seconds. The kneaded product was gradually fed into a Dome Gran DG-L1 (an extruder; Fuji Paudal Co., Ltd.) equipped with a dome-shaped die having a pore size of 0.6 mm and an aperture ratio of 22.6%. Extrusion was repeated three times at a screw speed of 40 rpm to produce fine noodle-like extrudates about 2 to 3 cm in length. Using a Marumerizer QJ-400 (a spheronizer; Fuji Paudal Co., Ltd.) equipped with a cross-hatch plate in which pitches are carved at intervals of 3 mm, the extrudates were processed for 20 seconds at a rotation speed of about 1000 rpm, producing wet pellets. The wet pellets were dried with an SPHH-200 (a tray oven; Tabai Espec Corp.) set at 70° C., for 2 to 3 hours to obtain dry pellets.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 19

| Wet-Kneaded Product | Measured Temperature |
| --- | --- |
| After Wet-Kneading | 22.9° C. |
| After 1$^{st}$ Extrusion | 28.1° C. |

TABLE 19-continued

| Wet-Kneaded Product | Measured Temperature |
| --- | --- |
| After 2$^{nd}$ Extrusion | 29.1° C. |
| After 3$^{rd}$ Extrusion | 31.5° C. |
| Temperature Difference Before and After 1$^{st}$ Extrusion | Δ 5.2° C. |

These results show that mixing trehalose dihydrate can impart moderate plasticity to a wet-kneaded product containing a large amount of methacrylic acid copolymer S.

Comparative Example 4

The amorphous tolvaptan (90 g; tolvaptan amount: 60 g) prepared in Reference Example 1, 15 g of Wyndale Lactose 200M (lactose monohydrate; The Lactose Company of New Zealand Limited), 30 g of Eudragit S100 (methacrylic acid copolymer S; Degussa AG), and 10 g of Ceolus PH-301 (crystalline cellulose; Asahi Kasei Chemicals Corp.) were fed into a Speed Kneader NSK-150 (a mixing granulator; Okada Seiko Co., Ltd.). Then, 20 g of 5 w/v % HPC-L aqueous solution (hydroxypropylcellulose; Nippon Soda Co., Ltd.) and 17.5 g of purified water were added as binder solutions and wet-kneaded for 140 seconds. The kneaded product was gradually fed into a Dome Gran DG-L1 (an extruder; Fuji Paudal Co., Ltd.) equipped with a dome-shaped die having a pore size of 0.6 mm and an aperture ratio of 22.6%. Extrusion was repeated two times at a screw speed of 40 rpm; however, the third extrusion was stopped because a large load was imposed on the DG-L1 and the current value of the motor changed significantly.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 20

| Wet-Kneaded Product | Measured Temperature |
| --- | --- |
| After Wet-Kneading | 23.6° C. |
| After 1$^{st}$ Extrusion | 42.6° C. |
| After 2$^{nd}$ Extrusion | 49.2° C. |
| After 3$^{rd}$ Extrusion | 56.5° C. (Suspended) |
| Temperature Difference Before and After 1$^{st}$ Extrusion | Δ 19.0° C. |

These results show that mixing lactose monohydrate fails to impart moderate plasticity to a wet-kneaded product containing a large amount of methacrylic acid copolymer S.

Example 17

The amorphous tolvaptan (180 g; tolvaptan amount: 120 g) prepared in Reference Example 1, 25.8 g of Sunmalt-S (maltose monohydrate; Sanwa Cornstarch Co., Ltd.), 54 g of Eudragit S100 (methacrylic acid copolymer S; Degussa AG), and 18 g of Ceolus PH-301 (crystalline cellulose; Asahi Kasei Chemicals Corp.) were fed into a Speed Kneader NSK-150 (a mixing granulator; Okada Seiko Co., Ltd.). Then, 60 g of 5 w/v % HPC-L aqueous solution (hydroxypropylcellulose; Nippon Soda Co., Ltd.) and 11 g of purified water were added as binder solutions and wet-kneaded for 180 seconds. The kneaded product was gradually fed into a Dome Gran DG-L1 (an extruder; Fuji Paudal Co., Ltd.) equipped with a dome-shaped die having a pore size of 0.8 mm and an aperture ratio of 22.5%. Extrusion was repeated six times at a screw speed of 40 rpm to produce fine noodle-like extrudates about 2 to 4 cm in length. Using a Marumerizer QJ-400 (a spheronizer; Fuji Paudal Co., Ltd.) equipped with a cross-hatch plate in which pitches are carved at intervals of 3 mm, the extrudates were processed for 30 seconds at a rotation speed of about 1000 rpm, producing wet pellets. The wet pellets were dried with an SPHH-200 (a tray oven; Tabai Espec Corp.) set at 70° C., for 2 hours to obtain matrix pellets. The matrix pellets were sieved to a size of 600 to 1000 μm.

1. Measurement of Particle Size Distribution

The particle size of the matrix pellets (about 5 g) was measured with a Robot Shifter RPS-95 (Seishin Enterprise Co., Ltd.) based on the particle size-measuring method (dry-sieving method) defined in General Tests in the Japanese Pharmacopoeia. The average particle size of the matrix pellets was 770 μm.

2. Measurement of Decomposition

The matrix pellets (140.4 g) obtained in Example 17 were mixed well with 0.6 g of light anhydrous silicic acid (Adsolider-101; Y.K.F Inc.). The mixture was then filled in a size No. 3 hypromellose capsule (QUALI-V capsule; Qualicaps Co., Ltd.) in an amount equivalent to 60 mg of tolvaptan. The matrix pellets-containing capsules were placed in a plastic container and stored at 60° C. for two weeks.

The matrix pellets as mentioned above was pulverized in a mortar and the amount equivalent to 30 mg of tolvaptan was taken out. Then, methanol was added thereto, and ultrasonic waves were applied to completely destroy the pellets. Methanol was further added thereto, and the mixture was filtered through a membrane filter with a pore size of about 0.5 μm. The resulting filtrate was applied to a LC-2010 CT system (high speed liquid chromatography; Shimadzu Corp.) with a measurement wavelength of 254 nm and a mobile phase (acetonitrile, water, and phosphoric acid in a volume ratio of 500/500/1) flow rate of about 1 ml, to check for the presence of a certain decomposition product, which is referred as the decomposition product A, hereinafter. The concentration of the decomposition product A was calculated by the area percentage method (the ratio of the peak area of the decomposition product A to the peak area of tolvaptan).

Examining the concentration of the decomposition product A before and after storage, the concentration of the decomposition product A was 0.01% immediately after production and 0.02% after being stored at 60° C. for two weeks. This revealed that the production of decomposition products was suppressed.

3. Dissolution Test

Using a dissolution test system DT-610 (Jasco Corp.), the evaluation of tolvaptan dissolution from the matrix pellet-containing capsule was performed in accordance with the second method of the dissolution test (the paddle method) of the Japanese Pharmacopoeia. Polysorbate 80 was added to a diluted McIlvaine buffer of pH 7.4 for a concentration of 1 w/v %. This solution (900 ml) was used as a dissolution test solution. The rotation speed of the paddle was 50 rpm, and two wavelengths of 268 nm and 350 nm were used as measured wavelengths.

The following table indicates the dissolution rate, and the difference in the dissolution rate before and after storage at 60° C. for two weeks (the "Δ Dissolution Rate" is calculated by subtracting the value after 60° C./two-week storage from the value immediately after production).

TABLE 21

| Sampling Time | Immediately after Production | After 60° C./2-Week Storage | ΔDissolution Rate |
|---|---|---|---|
| 0.5 Hour | 20.9% | 20.4% | 0.5% |
| 1 Hour | 58.4% | 58.6% | −0.2% |
| 2 Hours | 88.3% | 92.6% | −4.3% |

Table 21 shows that there was little change in the dissolution rate of tolvaptan from the matrix pellet-containing capsule obtained in Example 17 immediately after production and after 60° C./two-week storage. It shows that the stability of the solid preparation of the present invention is clearly excellent.

Comparative Example 5

The amorphous tolvaptan (45 g; tolvaptan amount: 30 g) prepared in Reference Example 1, 45 g of Pearlitol 50C (D-mannitol; Roquette), 30 g of Eudragit 5100 (methacrylic acid copolymer S; Degussa AG), and 10 g of Ceolus PH-301 (crystalline cellulose; Asahi Kasei Chemicals Corp.) were fed into a NMG-1L (Nara Model High Shear Mixer Granulator; Nara Machinery Co., Ltd.). Then, 40 g of mixture (weight ratio of 1:1) of 4 w/v % HPC-L aqueous solution (hydroxypropylcellulose; Nippon Soda Co., Ltd.) and 4 w/v % polysorbate 80 aqueous solution (polysorbate 80 (HM); NOF Corporation) were added as binder solutions and wet-kneaded for 30 seconds. The kneaded product was gradually fed into a Dome Gran DG-L1 (an extruder; Fuji Paudal Co., Ltd.) equipped with a dome-shaped die having a pore size of 0.6 mm and an aperture ratio of 22.6%. Extrusion was repeated three times at a screw speed of 40 rpm to produce fine noodle-like extrudates about 2 to 4 cm in length. Using a Marumerizer QJ-400 (a spheronizer; Fuji Paudal Co., Ltd.) equipped with a cross-hatch plate in which pitches are carved at intervals of 3 mm, the extrudates were processed for 60 seconds at a rotation speed of about 1000 rpm, producing wet pellets. The wet pellets were dried with an SPHH-200 (a tray oven; Tabai Espec Corp.) set at 70° C., for 2 hours to obtain matrix pellets. The matrix pellets were sieved to a size of 355 to 850 μm.

The particle size distribution was measured in the same manner as in Example 17, and the average particle size of the matrix pellets was 690 μm.

After measurement and the dissolution test of the decomposition product A were carried out on the matrix pellets immediately after production, the matrix pellets were placed in a glass airtight container and stored for one year at room temperature. Measurement and the dissolution test of the decomposition product A were carried out on these pellets after being stored for one year at room temperature. The matrix pellets after one-year storage at room temperature were placed again in a glass airtight container and further stored at 60° C. for two weeks. Then, measurement and the dissolution test of the decomposition product A were carried out on the matrix pellets after two-week storage at 60° C. The measurement of the decomposition product A was conducted in the same manner as in Example 17. The dissolution test was conducted in the following manner.

Dissolution Test

Using a dissolution test system DT-610 (Jasco Corp.), the evaluation of tolvaptan dissolution from the matrix pellets was performed in accordance with the second method of the dissolution test (the paddle method) of the Japanese Pharmacopoeia. Polysorbate 80 was added to a diluted McIlvaine buffer of pH 7.0 for a concentration of 1 w/v %. This solution (900 ml) was used as a dissolution test solution. The rotation speed of the paddle was 100 rpm, and two wavelengths of 268 nm and 350 nm were used as measured wavelengths.

Table 22 shows the measurement result of the decomposition product A.

TABLE 22

| Sample | Amount of Produced Decomposition Product A |
| --- | --- |
| Immediately after Production | 0.01% |
| After 1-year Storage at Room Temperature | 0.13% |
| After 2-week Storage at 60° C. | 0.48% |

Table 23 shows the dissolution test result. In the table, the "Δ Dissolution Rate" is calculated by subtracting the dissolution rate after two-week storage at 60° C. from the dissolution rate after one-year storage at room temperature.

TABLE 23

| Sampling Time | Immediately after Production | After 1-Year/ Room Temperature Storage | After 2-Week/60° C. Storage | Δ Dissolution Rate |
| --- | --- | --- | --- | --- |
| 0.5 Hour | 53.4% | 56.2% | 34.2% | 22.0% |
| 1 Hour | 98.0% | 81.4% | 52.9% | 28.5% |
| 2 Hours | 99.7% | 92.7% | 67.7% | 25.0% |

When the matrix pellets contained a plasticizer (polysorbate 80), the amount of produced decomposition product A increased remarkably, while the dissolution rate decreased significantly. In addition, during one-year storage at room temperature, the amount of produced decomposition product A increased, and dissolution showed retardation. These results demonstrate that the matrix pellets obtained in Comparative Example 5 were remarkably inferior in stability of dissolution with time.

Example 18

The amorphous tolvaptan (180 g; tolvaptan amount: 120 g) prepared in Reference Example 1, 25.8 g of Sunmalt-S (maltose monohydrate; Sanwa Cornstarch Co., Ltd.), 18 g of Eudragit S100 (methacrylic acid copolymer S; Degussa AG), and 18 g of Ceolus PH-301 (crystalline cellulose; Asahi Kasei Chemicals Corp.) were fed into a Speed Kneader NSK-150 (a mixing granulator; Okada Seiko Co., Ltd.). Then, 60 g of 5 w/v % HPC-L aqueous solution (hydroxypropylcellulose; Nippon Soda Co., Ltd.) and 15 g of purified water were added as binder solutions and wet-kneaded for 250 seconds. The kneaded product was gradually fed into a Dome Gran DG-L1 (an extruder; Fuji Paudal Co., Ltd.) equipped with a dome-shaped die having a pore size of 0.8 mm and an aperture ratio of 22.5%. Extrusion was repeated five times at a screw speed of 60 rpm to produce fine noodle-like extrudates about 2 to 3 cm in length. Using a Marumerizer QJ-400 (a spheronizer; Fuji Paudal Co., Ltd.) equipped with a cross-hatch plate in which pitches are carved at intervals of 3 mm, the extrudates were processed for 50 seconds at a rotation speed of about 1000 rpm, producing wet pellets. The wet pellets were dried with an SPHH-200 (a tray oven; Tabai Espec Corp.) set at 70° C., for 2 hours to obtain dry pellets. The dry pellets were sieved to a size of 600 to 1000 μm. The dry pellets contain 7.4 wt. % of methacrylic acid copolymer S.

Example 19

The amorphous tolvaptan (180 g; tolvaptan amount: 120 g) prepared in Reference Example 1, 25.8 g of Sunmalt-S (maltose monohydrate; Sanwa Cornstarch Co., Ltd.), 30 g of Eudragit S100 (methacrylic acid copolymer S; Degussa AG), and 18 g of Ceolus PH-301 (crystalline cellulose; Asahi Kasei Chemicals Corp.) were fed into a Speed Kneader NSK-150 (a mixing granulator; Okada Seiko Co., Ltd.). Then, 60 g of 5 w/v % HPC-L aqueous solution (hydroxypropylcellulose; Nippon Soda Co., Ltd.) and 8 g of purified water were added as binder solutions and wet-kneaded for 160 seconds. The kneaded product was gradually fed into a Dome Gran DG-L1 (an extruder; Fuji Paudal Co., Ltd.) equipped with a dome-shaped die having a pore size of 0.8 mm and an aperture ratio of 22.5%. Extrusion was repeated six times at a screw speed of 60 rpm to produce fine noodle-like extrudates about 10 cm in length. Using a Marumerizer QJ-400 (a spheronizer; Fuji Paudal Co., Ltd.) equipped with a cross-hatch plate in which pitches are carved at intervals of 3 mm, the extrudates were processed for 25 seconds at a rotation speed of about 1000 rpm, producing wet pellets. The wet pellets were dried with an SPHH-200 (a tray oven; Tabai Espec Corp.) set at 70° C., for 2 hours to obtain dry pellets. The dry pellets were sieved to a size of 600 to 1000 μm. The dry pellets contain 11.7 wt. % of methacrylic acid copolymer S.

Example 20

The amorphous tolvaptan (180 g; tolvaptan amount: 120 g) prepared in Reference Example 1, 25.8 g of Sunmalt-S (maltose monohydrate; Sanwa Cornstarch Co., Ltd.), 54 g of Eudragit S100 (methacrylic acid copolymer S; Degussa AG), and 18 g of Ceolus PH-301 (crystalline cellulose; Asahi Kasei Chemicals Corp.) were fed into a Speed Kneader NSK-150 (a mixing granulator; Okada Seiko Co., Ltd.). Then, 60 g of 5 w/v % HPC-L aqueous solution (hydroxypropylcellulose; Nippon Soda Co., Ltd.) and 11 g of purified water were added as binder solutions and wet-kneaded for 180 seconds. The kneaded product was gradually fed into a Dome Gran DG-L1 (an extruder; Fuji Paudal Co., Ltd.) equipped with a dome-shaped die having a pore size of 0.8 mm and an aperture ratio of 22.5%. Extrusion was repeated six times at a screw speed of 60 rpm to produce fine noodle-like extrudates about 3 to 5 cm in length. Using a Marumerizer QJ-400 (a spheronizer; Fuji Paudal Co., Ltd.) equipped with a cross-hatch plate in which pitches are carved at intervals of 3 mm, the extrudates were processed for 30 seconds at a rotation speed of about 1000 rpm, producing wet pellets. The wet pellets were dried with an SPHH-200 (a tray oven; Tabai Espec Corp.) set at 70° C., for 2 hours to obtain dry pellets. The dry pellets were sieved to a size of 600 to 1000 μm. The dry pellets contain 19.2 wt. % of methacrylic acid copolymer S.

Comparative Example 6

The amorphous tolvaptan (90 g; tolvaptan amount: 60 g) prepared in Reference Example 1, 12.9 g of Sunmalt-S (maltose monohydrate; Sanwa Cornstarch Co., Ltd.), and 18 g of Ceolus PH-301 (crystalline cellulose; Asahi Kasei Chemicals Corp.) were fed into a Speed Kneader NSK-150 (a mixing granulator; Okada Seiko Co., Ltd.). Then, 30 g of 5 w/v % HPC-L aqueous solution (hydroxypropylcellulose; Nippon Soda Co., Ltd.) and 6 g of purified water were added as binder solutions and wet-kneaded for 210 seconds. The kneaded product was gradually fed into a Dome Gran DG-L1 (an extruder; Fuji Paudal Co., Ltd.) equipped with a dome-shaped die having a pore size of 0.8 mm and an aperture ratio of 22.5%. Extrusion was repeated five times at a screw speed of 60 rpm to produce fine noodle-like extrudates about 1 to 2 cm in length. Using a Marumerizer QJ-400 (a spheronizer; Fuji Paudal Co., Ltd.) equipped with a cross-hatch plate in which pitches are carved at intervals of 3 mm, the extrudates were processed for 60 seconds at a rotation speed of about 1000 rpm, producing wet pellets. The wet pellets were dried with an SPHH-200 (a tray oven; Tabai Espec Corp.) set at 70° C., for 2 hours to obtain dry pellets. The dry pellets were sieved to a size of 600 to 1000 μm. The dry pellets do not contain methacrylic acid copolymer S.

Dissolution Test

Using a dissolution test system DT-610 (Jasco Corp.), the evaluation of tolvaptan dissolution from the matrix pellet was performed in accordance with the second method of the dissolution test (the paddle method) of the Japanese Pharmacopoeia. The following Test Solutions 1 and 2 were used.

Test Solution 1: 900 ml of solution in which polysorbate 80 was added to a first solution (pH 1.2) as the dissolution test solution of the Japanese Pharmacopoeia 15th edition, for a concentration of 1 w/v %

Test Solution 2: 900 ml of solution in which polysorbate 80 was added to a diluted McIlvaine buffer (pH 7.4), for a concentration of 1 w/v %

The rotation speed of the paddle for both solutions was 50 rpm, and two wavelengths of 268 nm and 350 nm were used as the measured wavelengths.

Table 24 shows the dissolution test results for Test Solution 1. The numerical value in the table indicates the average value of three tests.

TABLE 24

| Sampling Time | Comparative Example 6 | Example 18 | Example 19 | Example 20 |
|---|---|---|---|---|
| 0.5 Hour | 6.5% | 6.1% | 6.8% | 6.9% |
| 1 Hour | 11.8% | 10.8% | 11.9% | 11.6% |
| 2 Hours | 19.3% | 17.3% | 19.8% | 18.7% |

Under an acid condition of pH 1.2, there was no difference in the dissolution of the drug from the pellets, and any difference in the content ratio of the methacrylic acid polymer was not recognized.

Table 25 shows the dissolution test results for Test Solution 2. The value in the table indicates the average value of three tests.

TABLE 25

| Sampling Time | Comparative Example 6 | Example 18 | Example 19 | Example 20 |
|---|---|---|---|---|
| 0.5 Hour | 6.3% | 9.8% | 12.7% | 31.9% |
| 1 Hour | 11.5% | 18.5% | 30.1% | 72.1% |
| 2 Hours | 18.8% | 30.2% | 54.3% | 97.6% |

In the pH regions where methacrylic acid polymers were dissolved, dissolution accelerated according to the amount thereof; however, Comparative Example 6 showed the exact same dissolution tendency as in the acid condition.

Example 21

Phenyloin (100 g, Sigma-Aldrich), 60 g of Erythritol 100M (erythritol; Nikken Fine Chemicals Co., Ltd.), 15 g of Eudragit L100 (methacrylic acid copolymer L, Degussa AG), and 20 g of Ceolus PH-301 (crystalline cellulose; Asahi Kasei Chemicals Corp.) were fed into a Speed Kneader NSK-150 (a mixing granulator; Okada Seiko Co., Ltd.). Then, 40 g of 5 w/v % HPC-L aqueous solution (hydroxypropylcellulose; Nippon Soda Co., Ltd.) and 9.5 g of purified water were added as binder solutions and wet-kneaded for 150 seconds. The kneaded product was gradually fed into a Dome Gran DG-L1 (an extruder; Fuji Paudal Co., Ltd.) equipped with a dome-shaped die having a pore size of 0.6 mm and an aperture ratio of 22.6%. Extrusion was repeated three times at a screw speed of 40 rpm to produce fine noodle-like extrudates about 2 to 3 cm in length. Using a Marumerizer QJ-400 (a spheronizer; Fuji Paudal Co., Ltd.) equipped with a cross-hatch plate in which pitches are carved at intervals of 3 mm, the extrudates were processed for 10 seconds at a rotation speed of about 1000 rpm, producing wet pellets. The wet pellets were dried with an SPHH-200 (a tray oven; Tabai Espec Corp.) set at 70° C., for 2 hours to obtain dry pellets.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 26

| Wet-Kneaded Product | Measured Temperature |
|---|---|
| After Wet-Kneading | 24.9° C. |
| After $1^{st}$ Extrusion | 26.8° C. |
| After $2^{nd}$ Extrusion | 27.1° C. |
| After $3^{rd}$ Extrusion | 27.0° C. |
| Temperature Difference Before and After $1^{st}$ Extrusion | Δ 1.9° C. |

Example 22

Aspirin (acetylsalicylic acid, 100 g, Wako Pure Chemical Industries, Ltd.), 10 g of Lactitol LC-1 (lactitol; Nikken Fine Chemicals Co., Ltd.), 40 g of Eudragit L100D55 (dry methacrylic acid copolymer LD; Degussa AG), and 20 g of Ceolus PH-301 (crystalline cellulose; Asahi Kasei Chemicals Corp.) were fed into a Speed Kneader NSK-150 (a mixing granulator; Okada Seiko Co., Ltd.). Then, 40 g of 5 w/v % HPC-L aqueous solution (hydroxypropylcellulose; Nippon Soda Co., Ltd.) and 9 g of purified water were added as binder solutions and wet-kneaded for 130 seconds. The kneaded product was gradually fed into a Dome Gran DG-L1 (an extruder; Fuji Paudal Co., Ltd.) equipped with a dome-shaped die having a pore size of 0.6 mm and an aperture ratio of 19.3%. Extrusion was repeated three times at a screw speed of 40 rpm to produce fine noodle-like extrudates about 2 to 3 cm in length. Using a Marumerizer QJ-400 (a spheronizer; Fuji Paudal Co., Ltd.) equipped with a cross-hatch plate in which pitches are carved at intervals of 3 mm, the extrudates were processed for 30 seconds at a rotation speed of about 1000 rpm, producing wet pellets. The wet pellets were dried with an SPHH-200 (a tray oven; Tabai Espec Corp.) set at 70° C., for 2 hours to obtain dry pellets.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 27

| Wet-Kneaded Product | Measured Temperature |
|---|---|
| After Wet-Kneading | 25.0° C. |
| After 1$^{st}$ Extrusion | 32.6° C. |
| After 2$^{nd}$ Extrusion | 34.6° C. |
| After 3$^{rd}$ Extrusion | 34.6° C. |
| Temperature Difference Before and After 1$^{st}$ Extrusion | Δ 7.6° C. |

Example 23

Naproxen (15 g, Sigma-Aldrich), 30 g of Trehalose P (trehalose dihydrate; Hayashibara Biochemical Laboratories, Inc.), 40 g of Eudragit L100D55 (dry methacrylic acid copolymer LD; Degussa AG), and 30 g of Ceolus PH-301 (crystalline cellulose; Asahi Kasei Chemicals Corp.) were fed into a Speed Kneader NSK-150 (a mixing granulator; Okada Seiko Co., Ltd.). Then, 20 g of 5 w/v % HPC-L aqueous solution (hydroxypropylcellulose; Nippon Soda Co., Ltd.) and 4.5 g of purified water were added as binder solutions and wet-kneaded for 140 seconds. The kneaded product was gradually fed into a Dome Gran DG-L1 (an extruder; Fuji Paudal Co., Ltd.) equipped with a dome-shaped die having a pore size of 0.6 mm and an aperture ratio of 22.6%. Extrusion was repeated three times at a screw speed of 40 rpm to produce fine noodle-like extrudates about 4 to 5 cm in length. Using a Marumerizer QJ-400 (a spheronizer; Fuji Paudal Co., Ltd.) equipped with a cross-hatch plate in which pitches are carved at intervals of 3 mm, the extrudates were processed for 30 seconds at a rotation speed of about 1000 rpm, producing wet pellets. The wet pellets were dried with an SPHH-200 (a tray oven; Tabai Espec Corp.) set at 70° C., for 2 hours to obtain dry pellets.

Using a non-contact infrared thermometer IR-101 (Technoline Ltd.), the temperature of the kneaded product was measured after wet-kneading, and the temperature of the wet-kneaded product was measured after each extrusion. The results are shown in the following table.

TABLE 28

| Wet-Kneaded Product | Measured Temperature |
|---|---|
| After Wet-Kneading | 25.0° C. |
| After 1$^{st}$ Extrusion | 34.5° C. |
| After 2$^{nd}$ Extrusion | 35.9° C. |
| After 3$^{rd}$ Extrusion | 36.4° C. |
| Temperature Difference Before and After 1$^{st}$ Extrusion | Δ 9.5° C. |

Example 24

The dry pellets (196 g) obtained in Example 20 were mixed with 0.8 g of Adsolider-101 (silicon dioxide; Y.K.F Inc.), and 141 mg of the resulting pellets were filled in a size No. 3 hypromellose capsule. The capsule contains 60 mg of tolvaptan.

Example 25

The amorphous tolvaptan (180 g; tolvaptan amount: 120 g) prepared in Reference Example 1, 25.8 g of Sunmalt-S (maltose monohydrate; Sanwa Cornstarch Co., Ltd.), 30 g of Eudragit S100 (methacrylic acid copolymer S; Degussa AG), and 18 g of Ceolus PH-301 (crystalline cellulose; Asahi Kasei Chemicals Corp.) were fed into a Speed Kneader NSK-150 (a mixing granulator; Okada Seiko Co., Ltd.). Then, 60 g of 5 w/v % HPC-L aqueous solution (hydroxypropylcellulose; Nippon Soda Co., Ltd.) and 3 g of purified water were added as binder solutions and wet-kneaded for 180 seconds. The kneaded product was gradually fed into a Dome Gran DG-L1 (an extruder; Fuji Paudal Co., Ltd.) equipped with a dome-shaped die having a pore size of 0.8 mm and an aperture ratio of 22.5%. Extrusion was repeated four times at a screw speed of 60 rpm to produce fine noodle-like extrudates about 2 cm in length. Using a Marumerizer QJ-400 (a spheronizer; Fuji Paudal Co., Ltd.) equipped with a cross-hatch plate in which pitches are carved at intervals of 3 mm, the extrudates were processed for 60 seconds at a rotation speed of about 1000 rpm, producing wet pellets. The wet pellets were dried with an SPHH-200 (a tray oven; Tabai Espec Corp.) set at 70° C., for 4 hours. The dry pellets were sieved to produce pellets with a size of 780 μm. The pellets (179 g) were mixed with 0.8 g of Adsolider-101 (silicon dioxide; Y.K.F Inc.), and 129 mg of the resulting pellets were filled in a size No. 3 hypromellose capsule. The capsule contains 60 mg of tolvaptan.

Example 26

The amorphous tolvaptan (180 g; tolvaptan amount: 120 g) prepared in Reference Example 1, 25.8 g of Sunmalt-S (maltose monohydrate; Sanwa Cornstarch Co., Ltd.), 54 g of Eudragit S100 (methacrylic acid copolymer S; Degussa AG), and 30 g of Ceolus PH-301 (crystalline cellulose; Asahi Kasei Chemicals Corp.) were fed into a Speed Kneader NSK-150 (a mixing granulator; Okada Seiko Co., Ltd.). Then, 60 g of 5 w/v % HPC-L aqueous solution (hydroxypropylcellulose; Nippon Soda Co., Ltd.) and 16 g of purified water were added as binder solutions and wet-kneaded for 180 seconds. The kneaded product was gradually fed into a Dome Gran DG-L1 (an extruder; Fuji Paudal Co., Ltd.) equipped with a dome-shaped die having a pore size of 0.8 mm and an aperture ratio of 22.5%. Extrusion was repeated four times at a screw speed of 60 rpm to produce fine noodle-like extdudates about 2 cm in length. Using a Marumerizer QJ-400 (a spheronizer; Fuji Paudal Co., Ltd.) equipped with a cross-hatch plate in which pitches are carved at intervals of 3 mm, the extrudates were processed for 60 seconds at a rotation speed of about 1000 rpm, producing wet pellets. The wet pellets were dried with an SPHH-200 (a tray oven; Tabai Espec Corp.) set at 70° C., for 4 hours. The dry pellets were sieved to produce pellets with a size of 780 μm. The pellets (217 g) were mixed with 0.9 g of Adsolider-101 (silicon dioxide; Y.K.F Inc.), and 147 mg of the resulting pellets were filled in a size No. 3 hypromellose capsule. The capsule contains 60 mg of tolvaptan.

Dissolution Test Method

Using a dissolution test system NTR-6200A (Toyama Sangyo Co., Ltd.), the evaluation of tolvaptan dissolution from the capsules obtained in Examples 24, 25, and 26 was performed in accordance with the second method of the dissolution test (the paddle method) of the Japanese Pharmacopoeia. The following test solution was used.

Test Solution: 900 ml of solution in which polysorbate 80 was added to a second solution (pH 6.8) as the dissolution test solution of the Japanese Pharmacopoeia 15th edition, for a concentration of 1 w/v %

Measured Wavelength: λ1, 268 nm; λ2, 350 nm
Rotation Speed of Paddle: 100 rpm
Number of Samples: n=6
Sampling Time: 0.5, 1, 2, 3, 4, 6, 8, 10, and 12 hours
Calculation of Time for 50% Dissolution ($T_{50}$)

The time needed for 50% of tolvaptan to dissolve was estimated from FIG. 1.

TABLE 29

50% Dissolution Time of Examples 24, 25, and 26 ($T_{50}$)

| | Example 24 | Example 25 | Example 26 |
|---|---|---|---|
| $T_{50}$ | 3.72 hrs. | 4.28 hrs. | 7.03 hrs. |

Oral Administration Test

In order to confirm the sustained-release effect of the pharmaceutical solid preparation of the present invention, an oral administration test was conducted on healthy human subjects. Eighteen healthy men and women (18-45 years old) were randomized into an A group, a B group, and a C group of six people each. An incomplete crossover trial of three groups and four stages was carried out according to the following schedule.

TABLE 30

Dosage Schedule of Oral Administration Test

| Group | 1st Stage | 2nd Stage | 3rd Stage | 4th Stage |
|---|---|---|---|---|
| A | Immediate-Release Tablets, Administered in Fasting State Twice a Day | Example 24, Administered in Fasting State Once a Day | Example 25, Administered in Fasting State Once a Day | Example 25, Administered after Meal Once a Day |
| B | Immediate-Release Tablets, Administered in Fasting State Twice a Day | Example 26, Administered in Fasting State Once a Day | Example 24, Administered in Fasting State Once a Day | Example 24, Administered after Meal Once a Day |
| C | Immediate-Release Tablets, Administered in Fasting State Twice a Day | Example 25, Administered in Fasting State Once a Day | Example 26, Administered in Fasting State Once a Day | Example 26, Administered after Meal Once a Day |

In the first stage, immediate-release tablets were administered to every group in a fasting state twice a day. Two tablets, together containing a total of 45 mg of tolvaptan (one 30 mg tablet and one 15 mg tablet), were administered orally in a fasting state in the early morning; a 15 mg tablet was then administered orally after 8 hours. The daily tolvaptan dosage was 60 mg. In the second stage, the different capsules obtained in Examples 24, 25, and 26 were administered orally to each group in a fasting state. In the third stage, the capsules of Examples 24, 25, and 26, different from those administered in the second stage, were administered orally to every group in a fasting state. In the fourth stage, the same capsules of Examples 24, 25, and 26 as those administered in the third stage were administered orally after meals. The meals were high-fat foods arranged according to guidance from the U.S. FDA (Non-Patent Document 2). The capsules of Examples 24, 25, and 26 were administered orally within 30 minutes after each meal. The numbers of cases in which the immediate-release tablets and the capsules of Examples 24, 25, and 26 were administered under fasting conditions were 18 and 12, respectively, and the number of cases in which the capsules of Examples 24, 25, and 26 were administered after meals was six. The compositions of the immediate-release formulations are as follows.

Non-Patent Document 2: Guidance for Industry: Food-Effect Bioavailability and Fed Bioequivalence Studies., U.S. Department of Health and Human Services, Food and Drug Administration, and Center for Drug Evaluation and Research (CDER), December 2002.

Comparative Example 7

30 mg Tablet (Immediate-Release Tablet)

The amorphous tolvaptan (112.5 g; tolvaptan amount: 75 g) prepared in Reference Example 1, 185 g of lactose monohydrate, 50 g of corn starch, and 50 g of crystalline cellulose were mixed and fed into a fluidized bed granulating dryer (Multiplex MP-01; Powrex Corporation). Fluid bed granulation and drying were carried out using 200 g of 5 w/v % hydroxypropylcellulose aqueous solution with a hydroxypropoxyl-group content of 53 to 78 wt. %, and granulated materials were obtained. The granulated materials were mixed with 22.5 g of LH-11 (low-substituted hydroxypropyl cellulose) and 5 g of magnesium stearate to obtain granules for tablets. The granules were compressed with a rotary tableting machine (12HUK-AWC; Kikusui Seisakusho Ltd.) at a tableting pressure of 900 kg and a rotation speed of 40 rpm, into plane tablets about 174 mg in weight and 8 mm in diameter containing 30 mg of tolvaptan.

Comparative Example 8

15 mg Tablet (Immeidate-Release Tablet)

The amorphous tolvaptan (56.3 g; tolvaptan amount: 37.6 g) prepared in Reference Example 1, 256.3 g of lactose monohydrate, 50 g of corn starch, and 50 g of crystalline cellulose were mixed and fed into a fluidized bed granulating dryer (Multiplex MP-01; Powrex Corporation). Fluid bed granulation and drying were carried out using 200 g of 5 w/v % hydroxypropylcellulose aqueous solution with a hydroxypropoxyl-group content of 53 to 78 wt. %, and granulated materials were obtained. The granulated materials were mixed with 22.5 g of LH-11 (low-substituted hydroxypropyl cellulose) and 5 g of magnesium stearate to obtain granules for tablets. The granules were compressed with a rotary tableting machine (12HUK-AWC; Kikusui Seisakusho Ltd.) at a tableting pressure of 1000 kg and a rotation speed of 50 rpm, into plane tablets about 180 mg in weight and 8 mm in diameter containing 15 mg of tolvaptan.

Evaluation

Blood samples were periodically collected, and the tolvaptan concentration in plasma was measured. The pharmacokinetic parameter was calculated using WinNonlin software (ver. 4.0; Pharsight Corporation) and PSAG-CP software (Asmedica Co.).

Figure 2:
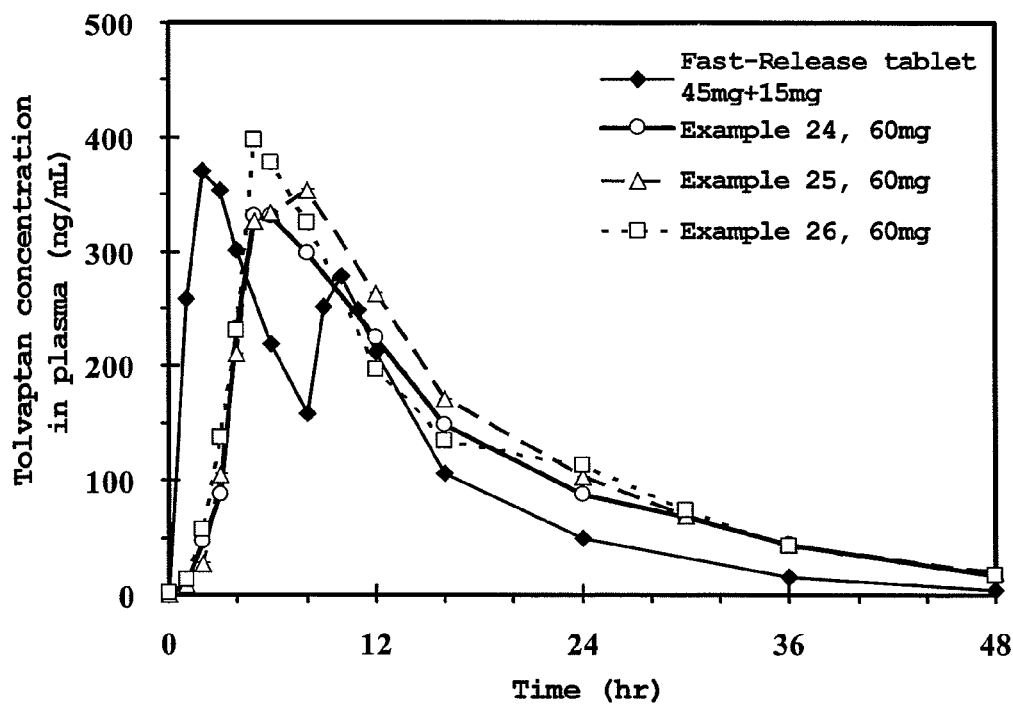
FIG. 2 shows tolvaptan plasma concentration after administration under fasting conditions.
Figure 3:
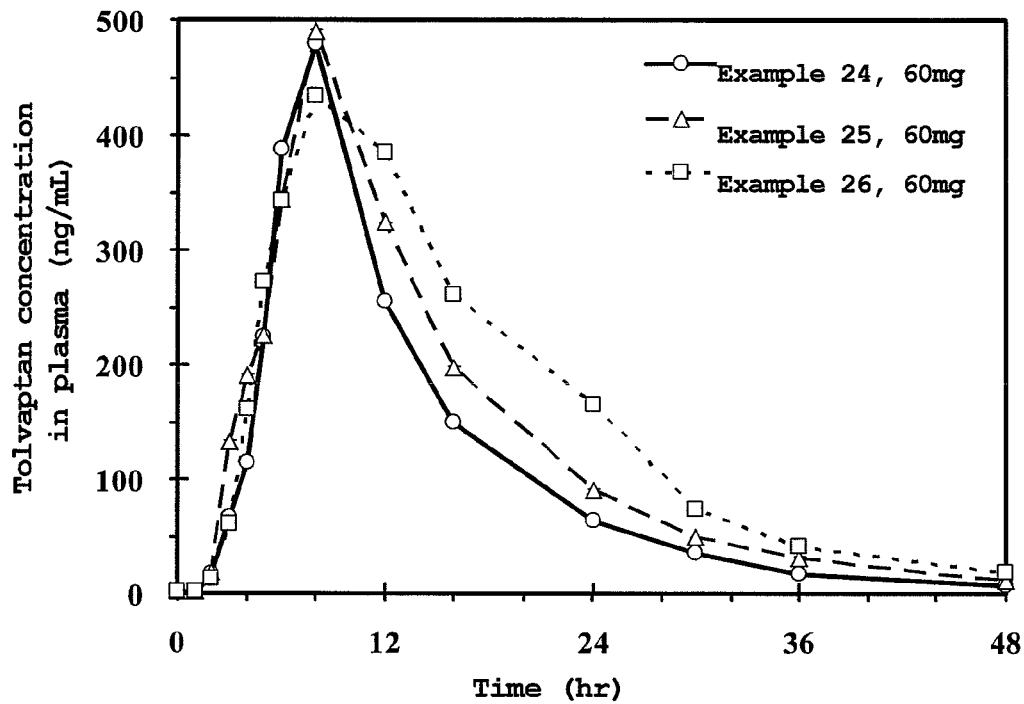
FIG. 3 shows tolvaptan plasma concentration after administration after meals.

FIG. 2 shows tolvaptan plasma concentration after administration under fasting conditions. FIG. 3 shows tolvaptan plasma concentration after administration after meals.

TABLE 31

PK Parameter of Each Administered Preparation in Oral Administration Test

| PK Parameter | Immediate-Release Tablet 45 mg + 15 mg | Example 24, 60 mg | Example 25, 60 mg | Example 26, 60 mg |
|---|---|---|---|---|
| Administered in Fasting State (Immediate-Release Tablet, n = 18; Examples 24-26, n = 12) | | | | |
| $C_{max}$ (ng/mL) | 414 ± 96.3 | 375 ± 168 | 385 ± 175 | 441 ± 168 |
| $AUC_\infty$ (ng · h/mL) | 4,840 ± 1,520 | 5,660 ± 1,730 | 6,300 ± 2,510 | 5,950 ± 1,990 |
| $t_{1/2}$ (h) | 7.6 ± 1.9 | 9.2 ± 1.9 | 10.1 ± 3.0 | 10.2 ± 3.1 |
| $C_{24\,hr}$ (ng/mL) | 49.5 ± 26.5 | 88.1 ± 41.0 | 102.8 ± 38.6 | 113.3 ± 90.4 |
| $MRT_t$ (h) | | 15.91 ± 3.64 | 15.84 ± 1.75 | 15.22 ± 2.60 |
| Administered After Meal (n = 6) | | | | |
| $C_{max}$ (ng/mL) | | 505 ± 80.8 | 507 ± 185 | 588 ± 102 |
| $AUC_\infty$ (ng · h/mL) | | 5,300 ± 1,580 | 6,349 ± 2,870 | 7,710 ± 2,430 |
| $t_{1/2}$ (h) | | 7.7 ± 1.4 | 7.5 ± 3.1 | 8.0 ± 1.8 |
| $C_{24\,hr}$ (ng/mL) | | 63.9 ± 34.9 | 90.3 ± 40.7 | 164.6 ± 83.9 |
| $MRT_t$ (h) | | 12.61 ± 1.90 | 13.91 ± 1.23 | 15.65 ± 2.82 |

Figure 4:
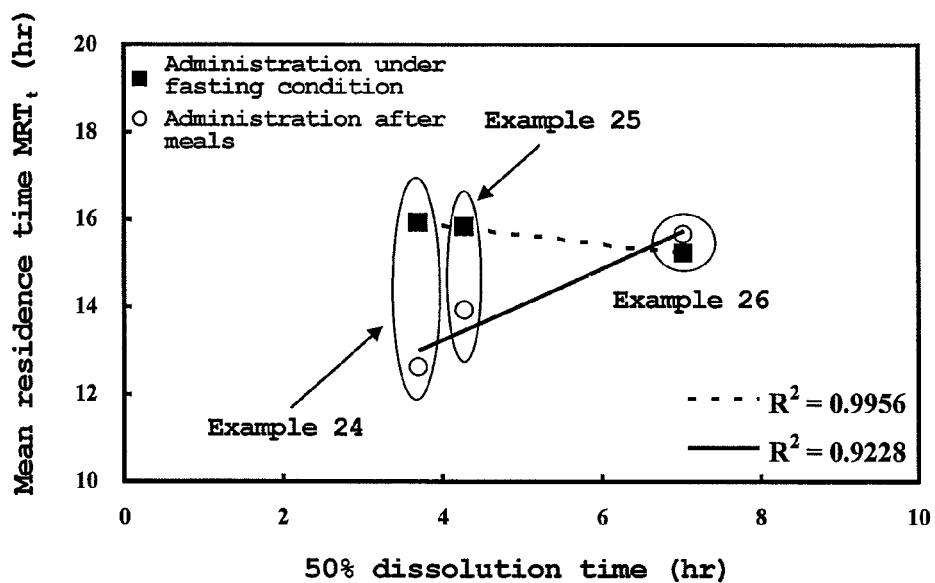
FIG. 4 shows diagrammatically the relationship between the mean residence time (MRT) and the 50% dissolution time ($T_{50}$) of Examples 24-26 (In Vitro-In Vivo Correlation).

FIG. 4 shows diagrammatically the relationship between the mean residence time (MRT) and the 50% dissolution time ($T_{50}$) of Examples 24-26 (In Vitro-In Vivo Correlation). The level B indicates well relationship between MRT and $T_{50}$ according to guidance from the U.S. FDA (Non-Patent Document 3).

Non-Patent Document 3: Guidance for Industry Extended Release Oral Dosage Forms: Development, Evaluation, and Application of In Vitro/In Vivo Correlations, U.S. Department of Health and Human Services, Food and Drug Administration, and Center for Drug Evaluation and Research (CDER), September 1997.

Color Tone Changes in Long-Term Storage Samples
Test Procedures

The pellets of Examples 13, 14, 15, and 16 were sealed in polyethylene bags and stored in a room for one year or more. The temperature and humidity at the conditions were not controlled. Changes in color tone were visually checked before and after storage. Additionally, the hardness of the pellets was checked by hand.

| Sample | Sugar/Sugar Alcohol | Color Tone | Pellet Hardness |
|---|---|---|---|
| Example 13 | Maltose Monohydrate | No Change | No Change |
| Example 14 | Erythritol | No Change | No Change |
| Example 15 | Lactitol Monohydrate | No Change | No Change |
| Example 16 | Trehalose Dihydrate | No Change | No Change |

There were no changes in the color tone or hardness of the granules in Examples 13 to 16.

INDUSTRIAL APPLICABILITY

The pharmaceutical solid preparation of the present invention serves many uses in the medical field. Particularly, the solid preparation can, without using a plasticizer, provide excellent plasticity to kneaded products during production. Further, the preparation can overcome the problems resulting from combining a plasticizer; the preparation is thus very useful. Moreover, the preparation has high utility value as an oral sustained-release pharmaceutical solid preparation.

The invention claimed is:

1. A matrix-type pharmaceutical solid preparation comprising:
    (a) a methacrylic acid-based enteric polymer;
    (b) a sugar and/or a sugar alcohol; and
    (c) tolvaptan,
    wherein the pharmaceutical solid preparation is free from a plasticizer,
    the pharmaceutical solid preparation is prepared by a production method including a wet-kneading process and an extrusion process,
    the tolvaptan (c) is amorphous and in powder form, and
    the sugar and/or the sugar alcohol (b) is at least one member selected from the group consisting of erythritol, xylitol, lactitol, sorbitol, trehalose, maltose, dextrose, fructose and maltitol.

2. The pharmaceutical solid preparation according to claim 1, wherein the amount of the sugar and/or the sugar alcohol is 0.1 to 10 parts by weight based on 1 part by weight of the methacrylic acid-based enteric polymer.

3. The pharmaceutical solid preparation according to claim 1, wherein the sugar and/or the sugar alcohol have a melting point of 140° C. or less.

4. The pharmaceutical solid preparation according to claim 2, wherein the sugar and/or the sugar alcohol have a melting point of 140° C. or less.

* * * * *